United States Patent
Buchwald

(10) Patent No.: US 10,562,848 B2
(45) Date of Patent: Feb. 18, 2020

(54) INHIBITORS OF TNF SUPERFAMILY COSTIMULATORY INTERACTIONS AND METHODS FOR USES OF THE SAME

(71) Applicant: UNIVERSITY OF MIAMI, Miami, FL (US)

(72) Inventor: Peter Buchwald, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/062,501

(22) PCT Filed: Dec. 15, 2016

(86) PCT No.: PCT/US2016/066821
§ 371 (c)(1),
(2) Date: Jun. 14, 2018

(87) PCT Pub. No.: WO2017/106436
PCT Pub. Date: Jun. 22, 2017

(65) Prior Publication Data
US 2018/0370909 A1    Dec. 27, 2018

Related U.S. Application Data

(60) Provisional application No. 62/267,712, filed on Dec. 15, 2015.

(51) Int. Cl.
| | |
|---|---|
| C07C 309/51 | (2006.01) |
| C07C 237/42 | (2006.01) |
| A61P 37/06 | (2006.01) |
| A61P 29/00 | (2006.01) |

(52) U.S. Cl.
CPC ............ *C07C 309/51* (2013.01); *A61P 29/00* (2018.01); *A61P 37/06* (2018.01); *C07C 237/42* (2013.01)

(58) Field of Classification Search
CPC . C07C 309/51; C07C 237/42; C07C 2603/18; A61P 29/00; A61P 37/06; C07D 249/18
See application file for complete search history.

(56) References Cited

U.S. PATENT DOCUMENTS

2011/0065675 A1    3/2011   Buchwald et al.

OTHER PUBLICATIONS

Fry, Biopolymers, Peptide Science, Protein-Protein Interactions as Targets for Small Molecule Drug Discovery, 2006, vol. 84, 535-552. (Year: 2006).*
Song et al, British Journal of Pharmacology, Small molecule modulators of the OX40-OX40 ligand co-stimulatory protein-protein interaction, 2014, 171, pp. 4955-4969. (Year: 2014).*
Aggarwal, Signalling pathways of the TNF superfamily: a double-edged sword, Nat. Rev. Immunol., 3(9):745-56 (Sep. 2003).
Arkin et al., Small-molecule inhibitors of protein-protein interactions: progressing toward the reality, Chem. Biol., 21(9):1102-14 (Sep. 2014).
Arkin et al., Small-molecule inhibitors of protein-protein interactions: progressing towards the dream, Nat. Rev. Drug Discov., 3(4):301-17 (Apr. 2004).
Berg, Modulation of protein-protein interactions with small organic molecules, Angew. Chem. Int. Ed. Engl., 42(22):2462-81 (Jun. 2003).
Bodmer et al., The molecular architecture of the TNF superfamily, Trends Biochem. Sci., 27(1):19-26 (Jan. 2002).
Bossen et al., Interactions of tumor necrosis factor (TNF) and TNF receptor family members in the mouse and human, J. Biol. Chem., 281(20):13964-71 (May 2006).
Buchwald, Small-molecule protein-protein interaction inhibitors: therapeutic potential in light of molecular size, chemical space, and ligand binding efficiency considerations, IUBMB Life, 62(10):724-31 (Oct. 2010).
Burkly, CD40 pathway blockade as an approach to immunotherapy, Adv. Exp. Med. Biol., 489:135-52 (2001).
Cechin et al., Effects of representative glucocorticoids on TNFa- and CD40L-induced NF-?B activation in sensor cells, Steroids, 85:36-43 (Jul. 2014).
Chen et al., Molecular mechanisms of T cell co-stimulation and co-inhibition, Nat. Rev. Immunol., 13(4):227-42 (Apr. 2013).
Croft et al., Clinical targeting of the TNF and TNFR superfamilies, Nat. Rev. Drug Discov., 12(2):147-68 (Feb. 2013).
Croft, Co-stimulatory members of the TNFR family: keys to effective T-cell immunity?, Nat. Rev. Immunol., 3(8):609-20 (2003).
Croft, The role of TNF superfamily members in T-cell function and diseases, Nat. Rev. Immunol., 9(4):271-85 (Apr. 2009).
Daoussis et al., Targeting CD40L: a promising therapeutic approach, Clin. Diagn. Lab Immunol., 11(4):635-41 (Jul. 2004).
Elgueta et al., Molecular mechanism and function of CD40/CD40L engagement in the immune system, Immunol. Rev., 229(1):152-72 (May 2009).
Frasca et al., Activation-Induced Cytidine Deaminase and Switched Memory B Cells as Predictors of Effective In Vivo Responses to the Influenza Vaccine, Methods Mol. Biol., 1343:107-14 (2015).

(Continued)

*Primary Examiner* — Paul A Zucker
(74) *Attorney, Agent, or Firm* — Marshall, Gerstein & Borun LLP

(57) ABSTRACT

Disclosed herein are inhibitors of TNF superfamily costimulatory interactions, and methods for their use in modulating TNF superfamily costimulatory interactions and treating immune system related disorders. In particular, disclosed herein are compounds of Formula (I), and pharmaceutically acceptable salts thereof:

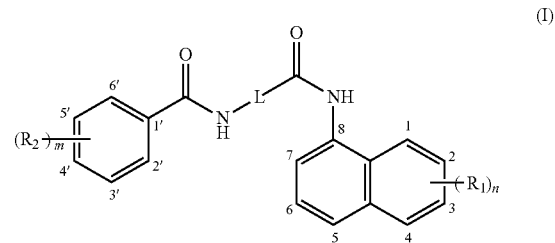

(I)

wherein the substituents are described herein.

20 Claims, 4 Drawing Sheets

(56) References Cited

OTHER PUBLICATIONS

Fry, Protein-protein interactions as targets for small molecule drug discovery, Biopolymers, 84(6):535-52 (2006).

Ganesan et al., The food colorant erythrosine is a promiscuous protein-protein interaction inhibitor, Biochem. Pharmacol., 81(6):810-8 (Mar. 2011).

Gao et al., Negative T cell costimulation and islet tolerance, Diabetes Metab. Res. Rev., 19(3):179-85 (May-Jun. 2003).

International Application No. PCT/US16/66821, International Preliminary Report on Patentability, dated Jun. 19, 2018.

International Application No. PCT/US16/66821, International Search Report and Written Opinion, dated Mar. 22, 2017.

Kassack et al., Structure-activity relationships of analogues of NF449 confirm NF449 as the most potent and selective known P2X1 receptor antagonist, Eur. J. Med. Chem., 39(4):345-57 (Apr. 2004).

Larsen et al., A new look at blockade of T-cell costimulation: a therapeutic strategy for long-term maintenance immunosuppression, Am. J. Transplant., 6(5 Pt 1):876-83 (May 2006).

Leader et al., Protein therapeutics: a summary and pharmacological classification, Nat. Rev. Drug Discov., 7(1):21-39 (Jan. 2008).

Li et al., Costimulatory pathways in transplantation: challenges and new developments, Immunol. Rev., 229(1):271-93 (May 2009).

Locksley et al., The TNF and TNF receptor superfamilies: integrating mammalian biology, Cell, 104(4):487-501 (Feb. 2001).

Margolles-Clark et al., Effective and specific inhibition of the CD40-CD154 costimulatory interaction by a naphthalenesulphonic acid derivative, Chem. Biol. Drug Des., 76(4):305-13 (Oct. 2010).

Margolles-Clark et al., Small-molecule costimulatory blockade: organic dye inhibitors of the CD40-CD154 interaction, J. Mol. Med. (Berl), 87(11):1133-43 (Nov. 2009).

Margolles-Clark et al., Suramin inhibits the CD40-CD154 costimulatory interaction: a possible mechanism for immunosuppressive effects, Biochem. Pharmacol., 77(7):1236-45 (Apr. 2009).

Meier et al., Can emerging drug classes improve R&D productivity?, Drug Discov. Today, 18(13-14):607-9 (Jul. 2013).

Mullard, Protein-protein interaction inhibitors get into the groove, Nat. Rev. Drug Discov., 11(3):173-5 (Mar. 2012).

Overington et al., How many drug targets are there?, Nat. Rev. Drug Discov., 5(12):993-6 (Dec. 2006).

Peters et al., CD40 and autoimmunity: the dark side of a great activator, Semin. Immunol., 21(5):293-300 (Oct. 2009).

Pinelli et al., An anti-CD154 domain antibody prolongs graft survival and induces Foxp3(+) iTreg in the absence and presence of CTLA-4 Ig, Am. J. Transplant., 13(11):3021-30 (Nov. 2013).

Pubmed Substance Record for SID 77675625, 8-[[4-[(3-nitrobenzoyl)amino]benzoyl]amino]naphthalene-1,3,6-trisulfonic Acid, U.S. National Library of Medicine, downloaded from the Internet at: <https://pubchem.ncbi.nlm.nih.gov/substance/77675625> (Jun. 12, 2009).

Quezada et al., CD40/CD154 interactions at the interface of tolerance and immunity, Annu. Rev. Immunol., 22:307-28 (2004).

Sathish et al., Challenges and approaches for the development of safer immunomodulatory biologics, Nat. Rev. Drug Discov., 12(4):306-24 (Apr. 2013).

Song et al., Small-molecule modulators of the OX40-OX40 ligand co-stimulatory protein-protein interaction, Br. J. Pharmacol., 171(21):4955-69 (Nov. 2014).

Song et al., TNF superfamily protein-protein interactions: feasibility of small-molecule modulation, Curr. Drug Targets, 16(4):393-408 (2015).

Tansey et al., The TNF superfamily in 2009: new pathways, new indications, and new drugs, Drug Discov. Today, 14(23-24):1082-8 (Oct. 2009).

Venkatraj et al., Synthesis and evaluation of non-basic inhibitors of urokinase-type plasminogen activator (uPA), Bioorg. Med. Chem., 20(4):1557-68 (Feb. 2012).

Verdine et al., The challenge of drugging undruggable targets in cancer: lessons learned from targeting BCL-2 family members, Clin. Cancer Res., 13(24):7264-70 (Dec. 2007).

Vincenti et al., T cell costimulation: a rational target in the therapeutic armamentarium for autoimmune diseases and transplantation, Annu. Rev. Med., 58:347-58 (2007).

Watts, TNF/TNFR family members in costimulation of T cell responses, Annu. Rev. Immunol., 23:23-68 (2005).

Weaver et al., Costimulation blockade: towards clinical application, Front Biosci., 13:2120-39 (Jan. 2008).

Wells et al., Reaching for high-hanging fruit in drug discovery at protein-protein interfaces, Nature, 450(7172):1001-9 (Dec. 2007).

Whitty et al., Between a rock and a hard place?, Nat. Chem. Biol., 2(3):112-8 (Mar. 2006).

Yao et al., Advances in targeting cell surface signalling molecules for immune modulation, Nat. Rev. Drug Discov., 12(2):130-46 (Feb. 2013).

\* cited by examiner

INHIBITORS OF TNF SUPERFAMILY COSTIMULATORY INTERACTIONS AND METHODS FOR USES OF THE SAME

STATEMENT OF GOVERNMENT SUPPORT

This invention was made with government support under grant number 1R01AI101041 awarded by the National Institutes of Health. The Government has certain rights in this invention.

FIELD OF THE DISCLOSURE

The present disclosure relates to novel, small molecule inhibitors of TNF superfamily costimulatory interactions, and methods of using the small molecules to modulate TNF superfamily costimulatory interactions and treat diseases.

BACKGROUND

Costimulatory signals play crucial roles in T cell biology as they determine the outcome of T cell receptor signaling (see Chen et al., Nat Rev Immunol 13: 227-242 (2013)). Blocking of the costimulatory protein-protein interaction is one of the most actively investigated pathways to mitigate immune responses in transplant patients and autoimmune diseases. According to the current knowledge, T cell activation is thought to require at least two signals: (1) engagement of the T cell receptor (TCR) with the MHC-peptide complex and (2) ligation of costimulatory molecules on T cells with their respective ligands on antigen-presenting cells (APCs). T cells receiving signal 1 and positive costimulation undergo proliferation, cytokine production, and further differentiate into effector cells. Even if the underlying mechanisms are not entirely understood, it is generally believed that antigen recognition in the absence of costimulation may alter the immune response and ultimately lead to tolerance.

Several cell surface receptor-ligand pairs provide important co-signaling (costimulatory as well as coinhibitory signaling) interactions that regulate T cell activation. The proteins involved in these cell surface interactions belong to two main families: the immunoglobulin superfamily (CD28-CD80/86 and ICOS-ICOS-L) and the tumor necrosis factor (TNF)-TNFR superfamily. Costimulation of T-cell activation has been reported for several members of the TNFR-TNF superfamily (see Locksley et al., Cell 104:487-501 (2001); Croft, Nat Rev Immunol 3:609-620 (2003); Watts, Annul Rev Immunol 23:23-68 (2005); Li et al., Immunol Rev 229:271-293 (2009); and Croft, Nat Rev Immunol 9:271-285 (2009)), and all its members play important roles in various aspects of the immune response (see Locksley et al., Cell 104:487-501 (2001); Aggarwal, Nat Rev Immunol 3:745-756 (2003); and Yao et al., Nat Rev Drug Discov 12:130-146 (2013)). Consequently, they are promising therapeutic targets in autoimmune diseases, in transplant recipients as well as in cancers (see Chen et al., Nat Rev Immunol 13: 227-242 (2013); Locksley et al., Cell 104:487-501 (2001); Aggarwal, Nat Rev Immunol 3:745-756 (2003); and Yao et al., Nat Rev Drug Discov 12:130-146 (2013)). Costimulatory blockade has emerged as a particularly valuable target for immune modulation both in transplant recipients and in autoimmune diseases since it might avoid the broad suppression of immunity caused by currently existing immunosuppressive agents (see Li et al., Immunol Rev 229:271-293 (2009); Gao et al., Diabetes Metab Res Rev 19:179-185 (2003); Larsen et al., am J Transplant 6:876-833 (2006); Vinceti et al., Annu Rev Med 58:347-358 (2007); Weaver et al., Front Biosci 13:2120-2139 (2008); and Peters et al., Semin Immunol 21:293-300 (2009)). Because members of this family are expressed only upon T-cell activation (with the exception of CD27), they are generally considered to play a particularly important role in the effector and memory phases of the immune response (see Li et al., Immunol Rev 229:271-293 (2009)).

The TNF superfamily (TNFSF) contains about thirty structurally related receptors (TNFSF-R) and about twenty protein ligands that bind to one or more of these receptors (see Locksley et al., Cell 104:487-501 (2001); Aggarwal, Nat Rev Immunol 3:745-756 (2003); Bodmer et al., Trends Biochem Sci 27:19-26 (2002); Bossen et al., J Biol Chem 281:13964-13971 (2006); Tansey et al., Drug Discov Today 14:1082-1088 (2009); and Croft et al., Nat Rev Drug Discov 12:147-168 (2013)). TNFSF ligands are soluble or membrane-anchored trimers that cluster their cell surface receptors to initiate signal transduction. These interactions are integral to communication and signaling systems involved in numerous physiological functions essential to inflammatory signaling, to the functioning of the immune and nervous system, to bone development, and others. There are biologics in clinical development for almost all of these interaction pairs (see Tansey et al., Drug Discov Today 14:1082-1088 (2009); and Croft et al., Nat Rev Drug Discov 12:147-168 (2013)). Currently, there are five biologics blocking TNF (TNFSF2) or LTα (TNFSF1) that are approved for treating various autoimmune and inflammatory disorders including rheumatoid arthritis (RA), psoriatic arthritis, juvenile idiopathic arthritis, psoriasis, ankylosing spondylitis, Crohn's disease and ulcerative colitis: etanercept (LTα, TNFSF1 and TNF, TNFSF2), infliximab, adalimumab, certolizumab pegol, and golimumab (TNF, TNFSF2). There are also biologics targeting other TNFSF members approved for clinical use: brentuximab vedotin (CD30L, TNFSF8) for Hodgkin's lymphoma and systemic anaplastic large cell lymphoma (sALCL); denosumab (RANKL, TNFSF11) for osteoporosis, and belimumab (BAFF, TNFSF13B) for systemic lupus erythematosus (SLE) and RA (see Croft et al., Nat Rev Drug Discov 12:147-168 (2013)). Within the TNF superfamily, the CD40-CD40L interaction is one of the most important and most extensively studied interactions. CD40 (TNFRSF5) and CD40L (CD154, TNFSF5) were, in fact, the first TNFSF costimulatory molecules to be identified. CD40-CD40L is a therapeutic target in many diseases due to its involvement in driving inflammatory events and autoimmunity, and the therapeutic effects of its inhibition are mainly due to the suppression of T and B cell mediated immune responses. Blocking of this protein-protein interaction is a proven highly effective immunomodulatory therapy (see Burkley, Adv Exp Med Biol 489:135-152 (2001); Quezada et al., Annu Rev Immunol 22:307-328 (2004); Daoussis et al., Clin Diagn Lab Immunol 11:635-641 (2004); and Elgueta et al., Immunol Rev 229:152-172 (2009)). Hence, there is considerable ongoing interest in targeting CD40L and/or CD40, and multiple antibodies have been developed and reached different phases of preclinical or clinical testing. Corresponding biologics in clinical development include PG102, ASKP1240/4D11, lucatumumab (HCD122), dacetuzumab (SGN 40), Chi Lob 7/4, and CP 870893 (see Croft et al., Nat Rev Drug Discov 12:147-168 (2013)).

Such antibodies (immunoglobulins) have the advantage of being highly specific for their targets and quite stable in human serum; however, they usually cannot reach intracellular targets (see Verdine et al., Clin Cancer Res 13:7264-

7270 (2007)) and, as all other protein therapies, are often hindered by solubility, route of administration, distribution, and stability problems as well as by the possibility of a strong immune response mounted against them (see Leader et al., Nat Rev Drug Discov 7:21-39 (2008)). For immunomodulatory biologics, a high incidence of additional unwanted adverse reactions (including serious infections, malignancy, cytokine release syndrome, anaphylaxis, hypersensitivity as well as immunogenicity) always looms as a hindrance in their development (see Sathish et al., Nat Rev Drug Discov 12:306-324 (2013)). While some of these are due to on-target interactions (i.e., exaggerated pharmacology), some (e.g., generation of neutralizing anti-drug antibodies and hypersensitivity reactions) are due to the inherent immunogenicity of biologics (see Sathish et al., Nat Rev Drug Discov 12:306-324 (2013)). For example, out of the 40 licensed immunomodulatory biologics, 18 have been associated with serious infections, including reactivation of bacterial, viral, fungal, and opportunistic infections. Traditional small-molecule drugs could provide a convenient alternative. However, small molecules were not pursued at all as possible PPI inhibitors for a long time as they were considered unlikely to be effective. This is because these interactions usually involve relatively large protein surfaces (1,500-3,000 Å$^2$) that also lack the well-defined binding pockets present on traditional targets of most existing drugs (G-protein coupled receptors—GPCRs, ion channels, enzymes) (see Buchwald, IUBMB Life 62:724-731 (2010)). During the last two decades, it has become increasingly clear that, at least in certain cases, small molecules can act as effective PPI modulators. Sufficiently effective small-molecule inhibitors have been identified for a few important PPIs and several candidates are in advanced clinical development (see Buchwald, IUBMB Life 62:724-731 (2010); Berg, Angew Chem Int Ed Engl 42:2462-2481 (2003); Arkin et al., Nat Rev Drug Discov 3:301-317 (2004); Wells et al., 450:1001-1009 (2007); Fry, Biopolymers 84:535-552 (2006); Whitty et al., Nat Chem Biol 2:112-118 (2006); Mullard, Nat Rev Drug Discov, 11:173-175 (2012); and Arkin et al., 21:1102-1114 (2014)). Intriguingly, some of the latest data suggest that if the initial hurdles can be overcome, small-molecule PPIIs actually tend to perform quite well in clinical development: While very few such PPIIs have made it to clinical trials, those that do have a better than average chance of success (see Meier et al., 18:607-609 (2013)). For example, in phase I, latest-generation PPIIs (those that have been in development between 2005 and 2012) had an 82% probability of success, compared to 54% for all new molecular entities (NMEs), and in phase II, their probability of success was 57% vs. 34% for all NMEs (see Meier et al., 18:607-609 (2013)).

Targeting of TNFSF costimulatory interaction in general and of the CD40-CD40L in particular with small molecule inhibitors is of special interest for those suffering from some autoimmune disease as well as for transplant recipients in general and for pancreatic islet transplant recipients in particular. The modulation of these interactions can be beneficial in pathogenic processes of chronic inflammatory diseases, such as autoimmune diseases, neurodegenerative disorders, graft-versus-host disease, cancer, and atherosclerosis. Autoimmune diseases include diseases such as rheumatoid arthritis, systemic lupus erythematosus (SLE), multiple sclerosis (MS), type I (juvenile) diabetes, mixed connective tissue disease MCTD, Celiac disease, Crohn's disease, Grave's disease, Sjögren's syndrome, dermatomyositis, psoriasis, neurodegenerative disorders, and others. Certain organic dyes and related compounds can effectively interfere with costimulatory protein-protein interactions such as the CD40-CD40L or the OX40-OX40L, and we have identified the first small-molecule compounds capable of modulating these interactions (see Margolles-Clark et al, J Mol Med 87:1133-1143 (2009); Margolles-Clark et al., Chem Biol Drug Des 76:305-313 (2010); Song et al., Br J Pharmacol 171:4955-4969 (2014); and U.S. Patent Application Publication No. US 2011/0065675). However, because of their dye nature, these compounds (e.g., direct red 80, crocein scarlet 7B, mordant brown, and chlorazol violet N) cannot be used as such for therapeutic applications.

Accordingly, there is a need for new small molecule compounds that can modulate TNFSF costimulatory interactions.

SUMMARY

Provided herein is a compound of Formula (I), or a pharmaceutically acceptable salt thereof:

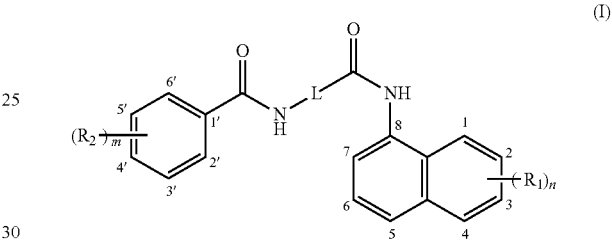

wherein:
L is fluorenyl, phenyl, or has a structure:

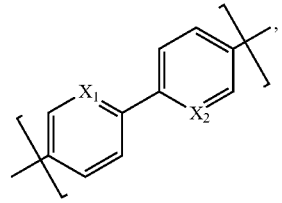

$X_1$ and $X_2$ are each independently CR or N; each $R_1$ independently is —SO$_3$H, —CO$_2$R, or —NO$_2$; each $R_2$ independently is —NO$_2$, —CO$_2$R, —NH$_2$, —Cl, —F, —CF$_3$, phenyl, or substituted phenyl, e.g., substituted with —NO$_2$, —CO$_2$R, —NH$_2$, —Cl, —F, or —CF$_3$, and/or two adjacent $R_2$ together form —(N=N—NH)—; each R independently is H, C$_{1-5}$ alkyl, or —O—C$_{1-5}$ alkyl; n is 1, 2, 3, or 4; and m is 1, 2, 3, or 4.

In some embodiments, L is phenyl. In various embodiments, L is fluorenyl. In some embodiments, L has a structure

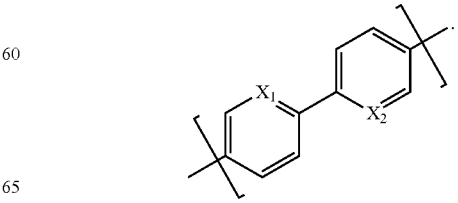

In some cases at least one of $X_1$ and $X_2$ is CR. In various cases, each of $X_1$ and $X_2$ is CR. In some embodiments, R is H. In some embodiments, R is $C_{1-5}$ alkyl. In some embodiments, R is —O—$C_{1-5}$ alkyl. In some cases, at least one of $X_1$ and $X_2$ is N. In various cases, each of $X_1$ and $X_2$ is N.

In some embodiments, at least one $R_1$ is $SO_3H$. In various embodiments, at least one $R_1$ is $CO_2R$. In some cases R is H. In various cases, R is $C_{1-5}$ alkyl. In some embodiments, when $R_1$ is $CO_2R$, R is not —O—$C_{1-5}$alkyl. In some embodiments, at least one $R_1$ is $NO_2$. In various embodiments, position 1 is substituted with $R_1$. In some embodiments, position 4 is substituted with $R_1$. In some embodiments, position 5 is substituted with $R_1$. In some cases $R_1$ is 1-$SO_3H$, 5-$SO_3H$, 4-$CO_2Me$, 5-$CO_2H$, or a combination thereof. For example, $R_1$ can be 1-$SO_3H$, 5-$CO_2H$, or a combination thereof.

In some embodiments, n is 1. In various embodiments, n is 2. In some embodiments, n is 3. In some embodiments, n is 4.

In some embodiments, at least one $R_2$ is —$NO_2$. In some embodiments, at least one $R_2$ is —$CO_2R$. In some cases R is H. In various cases, R is $C_{1-5}$ alkyl. In some embodiments, when $R_2$ is $CO_2R$, R is not —O—$C_{1-5}$alkyl. In various embodiments, at least one $R_2$ is —$NH_2$. In some embodiments, at least one $R_2$ is substituted phenyl. In some cases the phenyl is 4"-$NO_2$ substituted. In some cases, the phenyl is 4"-$CO_2R$ substituted. In various embodiments, at least one $R_2$ is —Cl. In some embodiments, at least one $R_2$ is —F. In various embodiments, at least one $R_2$ is —$CF_3$. In some embodiments, two adjacent $R_2$ together form —(N=N—NH)—. In some embodiments, position 4' is substituted with $R_2$. In various embodiments, position 3' is substituted with $R_2$. In various embodiments, $R_2$ is 4'-$NO_2$, 4'-$CO_2Me$, 4'-$NH_2$, or 3',4'—(N=N—NH)—. In some embodiments, $R_2$ is 4'-$NO_2$ or 4' $CO_2Me$.

In some embodiments, m is 1. In various embodiments, m is 2. In some embodiments, m is 3. In some embodiments, m is 4.

For example, the compound of formula (I) can be selected from the group consisting of:

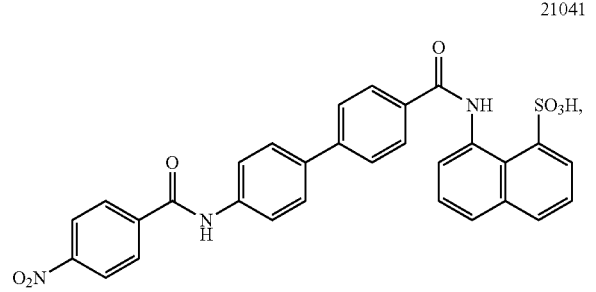
21041

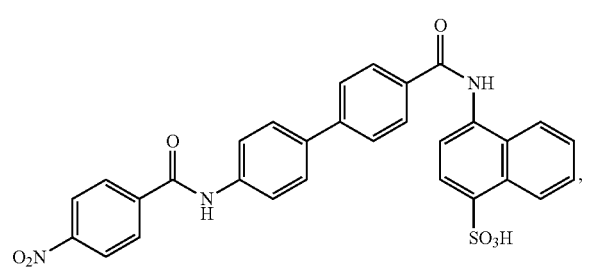
51041

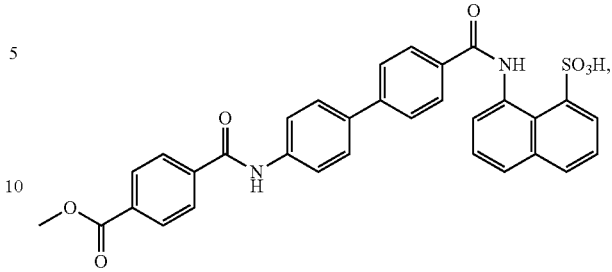
21045

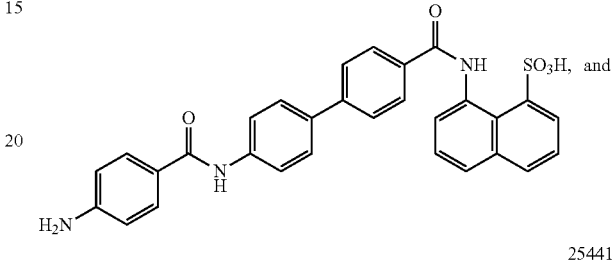
21042

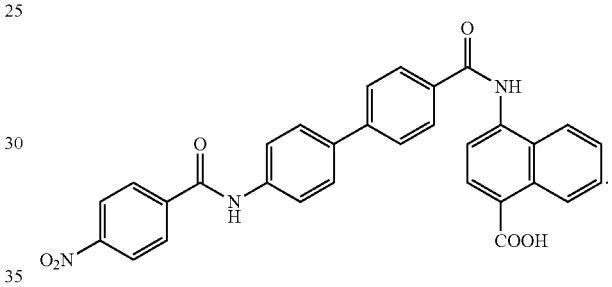
25441

Also provided is a pharmaceutical composition comprising a compound of Formula (I) or a pharmaceutically acceptable salt thereof, as described herein, and a pharmaceutically acceptable excipient. In some cases, the pharmaceutical composition comprises a compound 21041, 51041, 21045, 21042, 25441, or combinations thereof, and a pharmaceutically acceptable excipient.

Further provided is the use of a compound of Formula (I) or a pharmaceutically acceptable salt thereof as a medicament. In some embodiments, the compound of Formula (I) or pharmaceutically acceptable salt thereof is used to modulate TNF superfamily costimulatory interactions. In various embodiments, the TNF superfamily costimulatory interaction modulated is selected from the group consisting of CD40-CD40L, TNF-R1-TNF-α, CD80(B7)-CD28, CD80(B7)-CD152(CTLA4), CD86(B7-2)-CD28, CD86-CD152, CD27-CD70, CD137(4-1BB)-4-1BBL, HVEM-LIGHT (CD258), CD30-CD30L, GITR-GITRL, BAFF-R(CD268)-BAFF(CD257), RANK(CD265)-RANKL(CD254), OX40(CD134)-OX40L(CD252), and combinations thereof.

Also provided is a method of treating an immune system related disorder in a subject in need thereof, comprising administering to the subject a therapeutically effective amount of a compound of Formula (I) or a pharmaceutically acceptable salt thereof, as described herein, or a pharmaceutical composition comprising a compound of Formula (I) or a pharmaceutically acceptable salt thereof. In some embodiments the immune system related disorder is selected from the group consisting of systemic lupus erythematosus (SLE), multiple sclerosis (MS), type 1 (juvenile) diabetes, rheumatoid arthritis, mixed connective tissue disease (MCTD), Celiac disease, Crohn's disease, ulcerative colitis, Grave's disease, Sjögren's syndrome, dermatomyositis, psoriasis, scleroderma, polymyositis, vasculitis, Wegener's granulomatosis, alopecia areata, chronic inflammatory disease, autoimmune disease, neurodegenerative disorder, graft-versus-host disease, cancer, atherosclerosis and a rejection of nonautologous organ or cell transplant. In some embodiments, the immune system related disorder is selected from the group consisting of chronic inflammatory disease, autoimmune disease, neurodegenerative disorder, graft-versus-host disease, cancer, atherosclerosis and a rejection of nonautologous organ or cell transplant. In some embodiments, the subject suffers from chronic inflammatory disease. In various embodiments, the subject is a nonautologous organ or cell transplant recipient and suffers from rejection of the nonautologous organ or cell transplant. For example, the nonautologous organ or cell transplant is a pancreatic islet transplant.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1A:
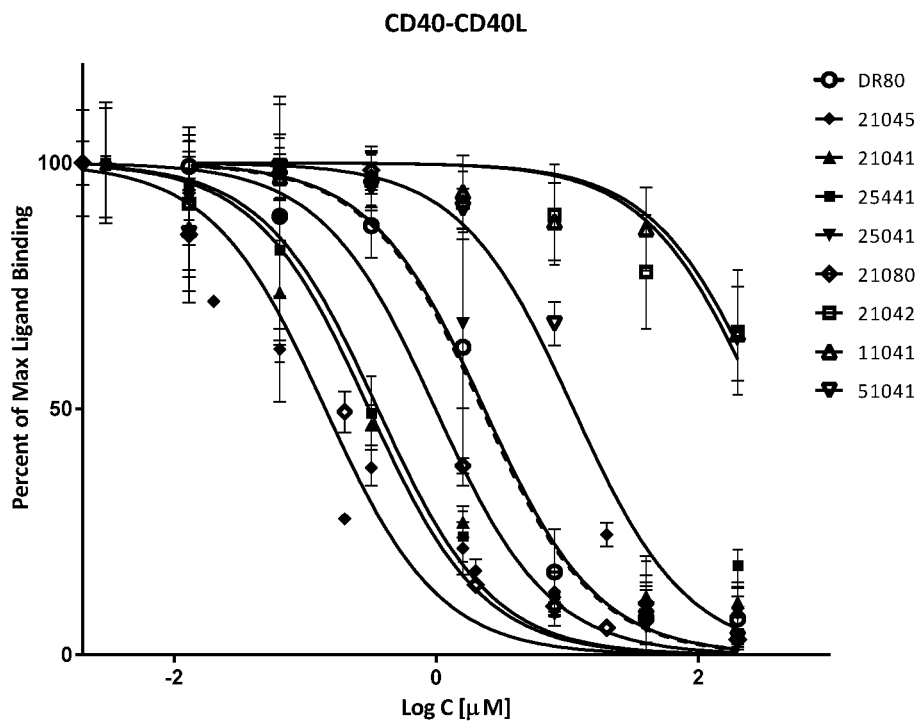
FIG. 1A shows concentration-dependent inhibition of human CD40-CD40L binding by 11041, 21041, 21042, 21045, 21080, 25041, 25441, and 51041 with direct red 80 (DR80) included as a positive control.

Disclosed herein are compounds and corresponding compositions containing the compounds that can modulate or interrupt TNFSF costimulatory interactions. The compounds and compositions disclosed herein can be used for immune suppression or tolerance induction in a recipient of a nonautologous organ or cell, or to treat or prevent autoimmune diseases. In some embodiments, the compounds disclosed herein demonstrate improved potency over other small molecule inhibitors such as direct red 80, crocein scarlet 7B, mordant brown, and chlorazol violet N which are active in the low µM range (see Margolles-Clark et al, J Mol Med 87:1133-1143 (2009); Margolles-Clark et al., Chem Biol Drug Des 76:305-313 (2010); and Song et al., Br J Pharmacol 171:4955-4969 (2014)).

In some cases, a compound disclosed herein exhibits a binding affinity for TNFSF or TNFSF-R in the range from about 100 nM (0.1 µM) to about 50 µM. In some embodiments, the binding affinity is about 100 nM to about 40 µM, about 100 nM to about 30 µM, about 100 nM to about 20 µM, about 100 nM to about 10 µM, about 100 nM to about 5 µM, about 100 nM to about 2.5 µM, about 100 nM to about 1 µM, or about 100 nm to about 500 nM.

The inhibitors disclosed herein have a structure of Formula (I), wherein the substituents are described in detail below.

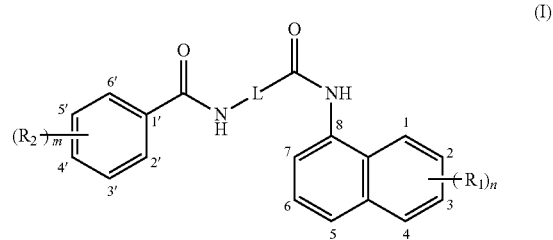

Definitions

As used herein, the term "alkyl" refers to straight chained and branched saturated hydrocarbon groups containing one to thirty carbon atoms, for example, one to twenty carbon atoms, one to ten carbon atoms, or one to five carbon atoms. The term $C_n$ means the alkyl group has "n" carbon atoms. For example, $C_4$ alkyl refers to an alkyl group that has 4 carbon atoms. $C_{1-5}$ alkyl refers to an alkyl group having a number of carbon atoms encompassing the entire range (i.e., 1 to 5 carbon atoms), as well as all subgroups (e.g., 1-4, 2-5, 1-3, 2-4, 3-4, 2-3, 1, 2, 3, 4, and 5 carbon atoms). Nonlimiting examples of alkyl groups include, methyl, ethyl, n-propyl, isopropyl, n-butyl, sec-butyl (2-methylpropyl), t-butyl (1,1-dimethylethyl), n-pentyl, 1,1-dimethylpropyl, 2,2-dimethylpropyl, 1,2-dimethylpropyl, 3-methylbutyl, 2-methylbutyl, 1-methylbutyl. Unless otherwise indicated, an alkyl group can be an unsubstituted alkyl group or a substituted alkyl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. The term "haloalkyl" refers to an alkyl group that is substituted with at least one halogen.

As used herein, the term "ether" refers to an "alkyl-O-alkyl" group. The ether group can be unsubstituted or substituted.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the terms "disease" and "disorder" may be used interchangeably.

As used herein, the term "pharmaceutically acceptable" means that the referenced substance, such as a compound of the present disclosure, or a formulation containing the compound, or a particular excipient, is safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment. In some cases, the treating refers to treating a symptom of a disorder or disease as disclosed herein.

As used herein, the term "excipient" means any pharmaceutically acceptable additive, carrier, diluent, adjuvant, or other ingredient, other than the active pharmaceutical ingredient (API).

As used herein, the term "modulate" means that a compound or composition as disclosed herein alters an interaction between a member of a TNF super family and a costimulatory agent. For example, a compound as disclosed herein can interrupt the interaction between one or more of the following: CD40-CD40L, TNF-R1-TNF-α, CD80(B7)-CD28, CD80(B7)-CD152(CTLA4), CD86(B7-2)-CD28, CD86-CD152, CD27-CD70, CD137(4-1BB)-4-1BBL, HVEM-LIGHT(CD258), CD30-CD30L, GITR-GITRL, BAFF-R(CD268)-BAFF(CD257), RANK(CD265)-RANKL(CD254), OX40(CD134)-OX40L(CD252).

As used herein "immune system related disorder" relates to diseases or disorders that result in over-activity of the immune system or in some cases abnormally low activity of the immune system. Specific immune system related disorders contemplated include systemic lupus erythematosus (SLE), multiple sclerosis (MS), type 1 (juvenile) diabetes, rheumatoid arthritis, mixed connective tissue disease (MCTD), Celiac disease, Crohn's disease, ulcerative colitis, Grave's disease, Sjögren's syndrome, dermatomyositis, psoriasis, scleroderma, polymyositis, vasculitis, Wegener's granulomatosis, alopecia areata, chronic inflammatory disease, autoimmune disease, neurodegenerative disorder, graft-versus-host disease, cancer, atherosclerosis and a rejection of nonautologous organ or cell transplant.

Small Molecule Inhibitors of TNF Superfamily Costimulatory Interactions

Provided herein are compounds of Formula (I), or pharmaceutically acceptable salts thereof:

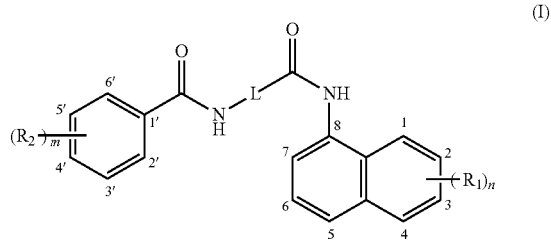

wherein:

L is fluorenyl, phenyl, or has a structure:

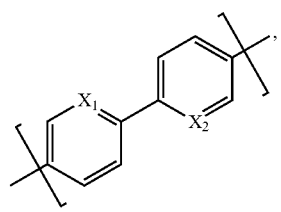

wherein $X_1$ and $X_2$ are each independently CR or N; each $R_1$ independently is —$SO_3H$, —$CO_2R$, or —$NO_2$; each $R_2$ independently is —$NO_2$, —$CO_2R$, —$NH_2$, —Cl, —F, —$CF_3$, phenyl, or substituted phenyl, e.g., substituted with —$NO_2$, —$CO_2R$, —$NH_2$, —Cl, —F, or —$CF_3$, and/or two adjacent $R_2$ together form —(N=N—NH)—; each R independently is H, $C_{1-5}$ alkyl, or —O—$C_{1-5}$ alkyl; n is 1, 2, 3, or 4; and m is 1, 2, 3, or 4.

In some embodiments, L is phenyl. In various embodiments, L is fluorenyl. In some embodiments, L has a structure

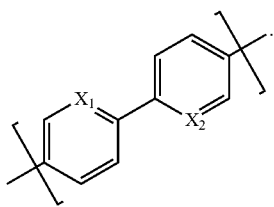

In some cases at least one of $X_1$ and $X_2$ is CR. In various cases, each of $X_1$ and $X_2$ is CR. In some embodiments, R is H. In some embodiments, R is $C_{1-5}$ alkyl. In some embodiments, R is —O—$C_{1-5}$ alkyl. In some cases R is selected from the group consisting of hydrogen, methyl, ethyl, n-propyl, isopropyl, n-butyl, and t-butyl. In some cases R is selected from the group consisting of hydrogen and methyl. In some cases, at least one of $X_1$ and $X_2$ is N. In various cases, each of $X_1$ and $X_2$ is N.

In some embodiments, at least one $R_1$ is $SO_3H$. In various embodiments, at least one $R_1$ is $CO_2R$. In some cases R is H. In various cases, R is $C_{1-5}$ alkyl. In some embodiments, when $R_1$ is $CO_2R$, R is not —O—$C_{1-5}$alkyl. In some cases R is selected from the group consisting of hydrogen, methyl, ethyl, n-propyl, isopropyl, n-butyl, and t-butyl. In some cases R is selected from the group consisting of hydrogen and methyl. In some embodiments, at least one $R_1$ is $NO_2$.

$R_1$ can suitably be positioned at any one or more of positions 1-7. In various embodiments, position 1 is substituted with $R_1$. In some cases, position 2 is substituted with $R_1$. In various embodiments, position 3 is substituted with $R_1$. In some embodiments, position 4 is substituted with $R_1$. In some embodiments, position 5 is substituted with $R_1$. In some cases, position 6 is substituted with $R_1$. In various embodiments, position 7 is substituted with $R_1$. In some cases, positions 1 and 2 are substituted with $R_1$. In some cases, positions 1 and 3 are substituted with $R_1$. In some cases, positions 1 and 4 are substituted with $R_1$. In some cases, positions 1 and 5 are substituted with $R_1$. In some cases, positions 1 and 6 are substituted with $R_1$. In some cases, positions 1 and 7 are substituted with $R_1$. In some cases, positions 2 and 3 are substituted with $R_1$. In some cases, positions 2 and 4 are substituted with $R_1$. In some cases, positions 2 and 5 are substituted with $R_1$. In some cases, positions 2 and 6 are substituted with $R_1$. In some cases, positions 2 and 7 are substituted with $R_1$. In some cases, $R_1$ is at least one of 1-$SO_3H$, 2-$SO_3H$, 3-$SO_3H$, 4-$SO_3H$, 5-$SO_3H$, 6-$SO_3H$, and/or 7-$SO_3H$. In some cases, $R_1$ is at least one of 1-$CO_2R$, 2-$CO_2R$, 3-$CO_2R$, 4-$CO_2R$, 5-$CO_2R$, 6-$CO_2R$, and/or 7-$CO_2R$. In some cases $R_1$ is 1-$SO_3H$, 5-$SO_3H$, 4-$CO_2Me$, 5-$CO_2H$, or a combination thereof. For example, $R_1$ can be 1-$SO_3H$, 5-$CO_2H$, or a combination thereof.

In some embodiments, n is 1. In various embodiments, n is 2. In some embodiments, n is 3. In some embodiments, n is 4.

In some cases R is H. In various cases, R is $C_{1-5}$ alkyl. In some cases, R is —O—$C_{1-5}$ alkyl. In some cases R is selected from the group consisting of hydrogen, methyl, ethyl, n-propyl, isopropyl, n-butyl, and t-butyl. In some cases R is selected from the group consisting of hydrogen and methyl.

In some embodiments, at least one $R_2$ is —$NO_2$. In some embodiments, at least one $R_2$ is —$CO_2R$. In some embodiments, when $R_2$ is $CO_2R$, R is not —O—$C_{1-5}$alkyl. In various embodiments, at least one $R_2$ is —$NH_2$. In some embodiments, at least one $R_2$ is substituted phenyl. In some cases, the phenyl is 4"-$NO_2$ substituted. In some cases, the phenyl is 4"-$CO_2R$ substituted. In some embodiments, when the phenyl is $CO_2R$ substituted, R is not —O—$C_{1-5}$alkyl. In various embodiments, at least one $R_2$ is a halogen. For example, in some embodiments at least one $R_2$ is —Cl. In some cases, at least one $R_2$ is —F. In various embodiments, at least one $R_2$ is —$CF_3$. In some embodiments, two adjacent $R_2$ together form —(N═N—NH)—.

$R_2$ can suitably be positioned at any one or more of positions 2' to 6'. In some embodiments, position 2' is substituted with $R_2$. In various embodiments, position 5' is substituted with $R_2$. In some embodiments, position 4' is substituted with $R_2$. In various embodiments, position 3' is substituted with $R_2$. In some embodiments, position 6' is substituted with $R_2$. In some cases, $R_2$ is at least one of 2'-$NO_2$, 3'-$NO_2$, 4'-$NO_2$, 5'-$NO_2$, and/or 6'-$NO_2$. In various embodiments, $R_2$ is at least one of 2'-$CO_2R$, 3'-$CO_2R$, 4'-$CO_2R$, 5'-$CO_2R$, and/or 6'-$CO_2R$. In some embodiments, $R_2$ is a para-substituted phenyl such as 4'-$C_6H_4$(4"-$NO_2$). In some embodiments, $R_2$ is a para-substituted phenyl such as 4'-$C_6H_4$(4"-$CO_2R$). In some cases R is selected from the group consisting of hydrogen, methyl, ethyl, n-propyl, isopropyl, n-butyl, and t-butyl. In some cases R is selected from the group consisting of hydrogen and methyl. In some embodiments, $R_2$ is at least one of 2'-$NH_2$, 3'-$NH_2$, 4'-$NH_2$, 5'-$NH_2$, and/or 6'-$NH_2$. In various embodiments, $R_2$ is at least one of 2'-halo, 3'-halo, 4'-halo, 5'-halo, and/or 6'-halo. In some cases, halo is selected from the group consisting of F, Cl, Br, and I. In some cases, halo is selected from the group consisting of F and Cl. In some embodiments, $R_2$ is at least one of 2$CF_3$, 3'-$CF_3$, 4'-$CF_3$, 5'-$CF_3$, and/or 6'-$CF_3$. In some cases, $R_2$ is at least one of 2',3'-(N═N—NH)—, 3',4'-(N═N—NH)—, 4',5'-(N═N—NH)—, and/or 5',6'—(N═N—NH)—. In various embodiments, $R_2$ is 4'-$NO_2$, 4'-$CO_2Me$, 4'-$NH_2$, or 3',4'-(N═N—NH)—. In some embodiments, $R_2$ is 4'-$NO_2$ or 4' $CO_2Me$.

When $R_2$ is substituted phenyl, the substitution can suitably be positioned at any one or more of positions 2" to 6". In some embodiments, position 2" is substituted. In some embodiments, position 3" is substituted. In some embodiments, position 4" is substituted. In some embodiments, position 5" is substituted. In some embodiments, position 6" is substituted. In various embodiments, the phenyl substitution is selected from the group consisting of with —$NO_2$, —COR, —$NH_2$, —Cl, —F, or —$CF_3$.

In some embodiments, m is 1. In various embodiments, m is 2. In some embodiments, m is 3. In some embodiments, m is 4.

For example, the compound of formula (I) can be selected from the group consisting of:

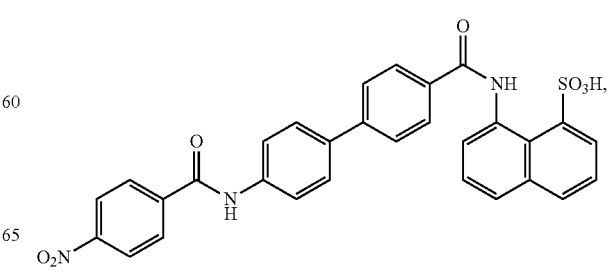

21041

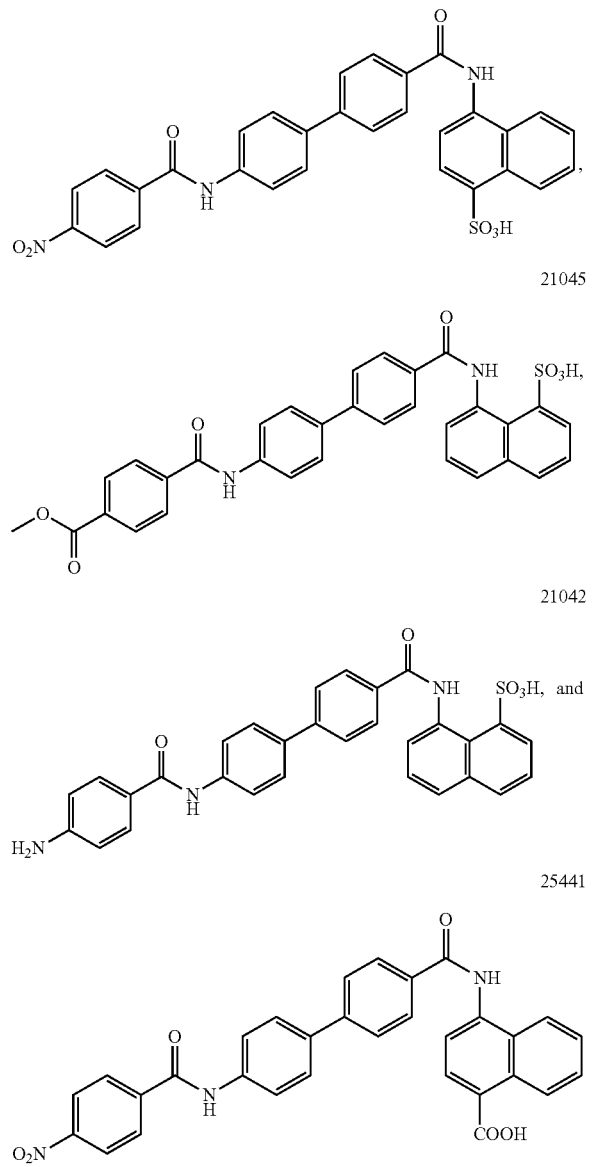

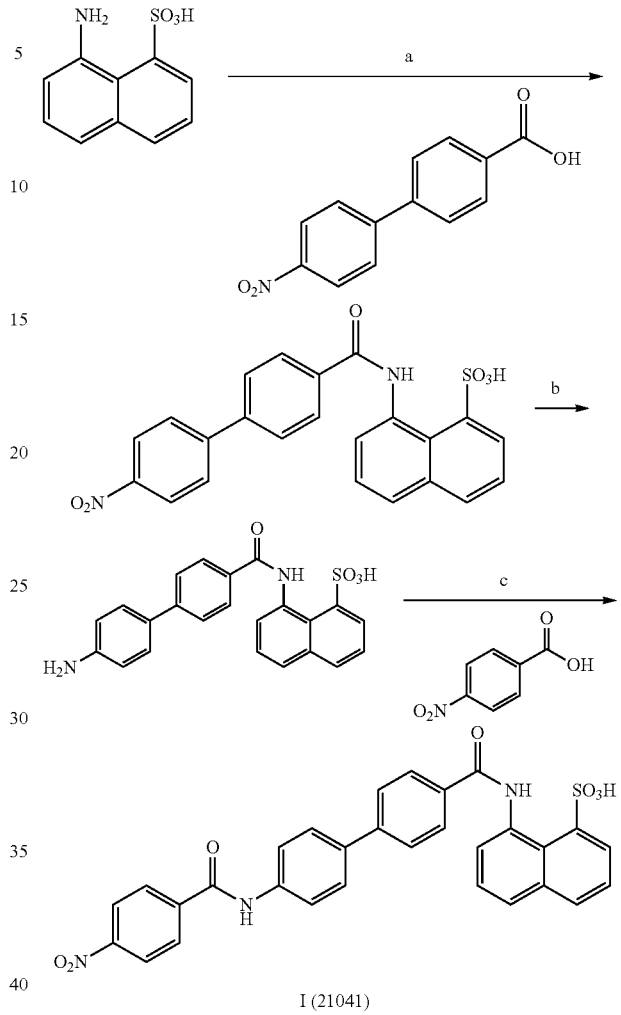

Scheme 1:

I (21041)

Synthesis of Inhibitors of TNF Superfamily Costimulatory Interactions

The inhibitors described herein can be synthesized by any method known to one skilled in the art. For example, three steps consisting of two amide couplings and one hydrogenation (Scheme 1). In particular, for example, 8-amino-1-naphthalenesulfonic acid can be coupled with 4'-nitrobiphenyl-4-carboxylic acid (Scheme 1, step a) to form an intermediate, 8-[(4'-nitrobiphenyl-4-yl-carbonyl)amino]naphthalene-1-sulphinic acid. This intermediate can then be reduced to the corresponding amine, 8-[(4'-aminobiphenyl-4-yl-carbonyl)amino]naphthalene-1-sulphinic acid (Scheme 1, step b), which, in turn, can be coupled with 4-nitrobenzoic acid (Scheme 1, step c) to form a compound of Formula (I), 8-(4'-(4-nitrobenzamido)biphenyl-4-ylcarboxamido)naphthalene-1-sulphinic acid (21041).

It will be appreciated that other compounds of Formula I can be prepared using a similar reaction scheme, modifying for starting reagents having the appropriate substitutions, and protecting and deprotecting reactive groups as necessary. Additional synthetic procedures for preparing the inhibitors disclosed herein can be found in the Examples section.

Methods

The compounds disclosed herein can modulate TNF superfamily costimulatory interactions, which is useful in treating inflammatory or immune system related disorders. Thus, provided herein is the use of a compound of Formula (I) or a pharmaceutically acceptable salt thereof, or a pharmaceutical composition comprising a compound of Formula (I) or a pharmaceutically acceptable salt thereof as a medicament.

Further provided are methods of modulating TNF superfamily costimulatory interactions and treating an inflammatory or immune system related disorder in a subject in need thereof, using a compound of Formula (I) or a pharmaceutically acceptable salt thereof, as disclosed herein.

Thus, provided herein is the use of a compound of Formula (I) or a pharmaceutically acceptable salt or composition thereof to modulate TNF superfamily costimulatory interactions. In various embodiments, the TNF superfamily costimulatory interaction modulated is selected from the group consisting of CD40-CD40L, TNF-R1-TNF-α, CD80 (B7)-CD28, CD80(B7)-CD152(CTLA4), CD86(B7-2)-CD28, CD86-CD152, CD27-CD70, CD137(4-1BB)-4-1BBL, HVEM-LIGHT(CD258), CD30-CD30L, GITR-GITRL, BAFF-R(CD268)-BAFF(CD257), RANK (CD265)-RANKL(CD254), OX40(CD134)-OX40L (CD252), and combinations thereof.

As discussed above, TNF superfamily costimulatory interactions are implicated immune responses. Thus, further provided is a method of treating an immune system related disorder in a subject, such as a human, in need thereof, comprising administering to the subject a therapeutically effective amount of a compound of Formula (I) or a pharmaceutically acceptable salt thereof, as described herein, or a pharmaceutical composition comprising a compound of Formula (I) or a pharmaceutically acceptable salt or composition thereof. In some embodiments, the inflammatory or immune system related disorder is selected from the group consisting of systemic lupus erythematosus (SLE), multiple sclerosis (MS), type 1 (juvenile) diabetes, rheumatoid arthritis, mixed connective tissue disease (MCTD), Celiac disease, Crohn's disease, ulcerative colitis, Grave's disease, Sjögren's syndrome, dermatomyositis, psoriasis, scleroderma, polymyositis, vasculitis, Wegener's granulomatosis, alopecia areata, chronic inflammatory disease, autoimmune disease, neurodegenerative disorder, graft-versus-host disease, cancer, atherosclerosis and a rejection of nonautologous organ or cell transplant. In some embodiments, the immune system related disorder is selected from the group consisting of chronic inflammatory disease, autoimmune disease, neurodegenerative disorder, graft-versus-host disease, cancer, atherosclerosis and a rejection of nonautologous organ or cell transplant. In some embodiments, the subject suffers from chronic inflammatory disease. In various embodiments, the subject is a nonautologous organ or cell transplant recipient and suffers from rejection of the nonautologous organ or cell transplant. For example, the nonautologous organ or cell transplant is a pancreatic islet transplant.

Pharmaceutical Formulations

Also provided herein are pharmaceutical compositions comprising a compound of Formula (I) or a pharmaceutically acceptable salt thereof, as previously described herein, and one or more pharmaceutically acceptable excipients.

The inhibitors described herein can be administered to a subject in a therapeutically effective amount. An inhibitor can be administered alone or as part of a pharmaceutically acceptable composition or formulation. In addition, an inhibitor can be administered all at once, multiple times, or delivered substantially uniformly over a period of time. It is also noted that the dose of the compound can be varied over time.

A compound disclosed herein can be administered to a patient or subject by any suitable route, e.g. orally, rectally, parenterally (for example, intravenously, intramuscularly, or subcutaneously), intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil), synthetic aliphatic acid glycerides, and esters of higher aliphatic acids such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, solubilizing, suspending, stabilizing, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, e.g., corn starch or potato starch, lactose, sucrose, mannitol, and silicic acid; (b) binders, as for example, crystalline cellulose, cellulose derivatives, carboxymethylcellulose, alginates, corn starch, gelatin, polyvinylpyrrolidone, sucrose, and acacia; (c) humectants, as for example, glycerol; (d) disintegrating agents, as for example, agar-agar, calcium carbonate, potato, corn, or tapioca starch, alginic acid, sodium carboxymethyl cellulose, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In some embodiments the solid dosage forms optionally include diluents, buffering agents, moistening agents, preservatives, and flavoring agents. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with bases such as emulsifying bases or water-soluble bases, or with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

In cases of compositions for inhalations or aerosol preparations, the compounds of the disclosure in the form of a liquid or minute powder may be filled up in an aerosol container with gas or liquid spraying agents, and if desired, together with conventional adjuvants such as humidifying agents. Compounds of the disclosure may also be formulated as pharmaceuticals for non-pressured preparations such as in a nebulizer or an atomizer.

A compound described herein can be administered to a patient or subject at dosage levels suitable to the intended use. The specific dosage and dosage range that will be used can potentially depend on a number of factors, including the requirements of the patient or subject, the severity of the disease or disorder being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

Example 1: Preparation of 8-[(4'-[4-nitrobenzamido]biphenyl-4-yl-carbonyl)amino]naphthalene-1-sulfonic acid (A Compound of Formula I, 21041)

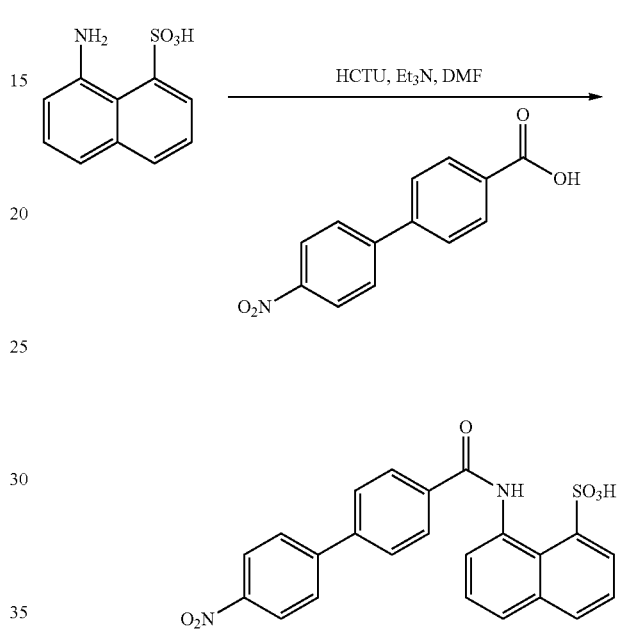

Coupling was performed following a general procedure that is a modified version of the procedure from Venkatraj, M. et al. Bioorg. Med. Chem. 20:1557-1568 (2012). Under an argon atmosphere, trimethylamine (Et$_3$N) was added dropwise to a mixture of 4'-nitrobiphenyl-4-carboxylic acid, O-(6-chlorobenzotriazol-1-yl)-N,N,N',N'-tetramethyluronium hexafluorophosphate (HCTU), and dimethylformamide (DMF) at 0° C. and the resulting reaction mixture was stirred for 1 h at the same temperature. Subsequently, 8-amino-1-naphthalenesulfonic acid was added at the same temperature. The resulting reaction mixture was allowed to stir overnight at room temperature. Diethyl ether was added to the reaction mixture, and a yellow precipitate formed. This precipitate was collected by filtration and washed with diethyl ether to afford the triethylamine salt of 8-(4'-nitrobiphenyl-4-ylcarboxamido)naphthalene-1-sulfonic acid as a yellow solid (66%). HRMS (ESI) [M+H]$^+$ calcd. for C$_{23}$H$_{17}$N$_2$O$_6$S$^+$, 449.0802; found, 449.0781.

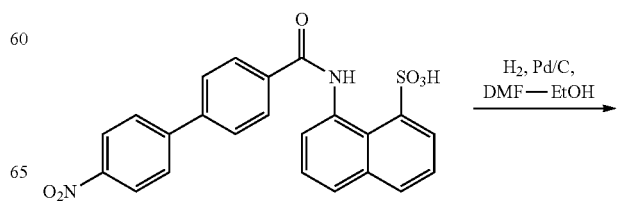

-continued

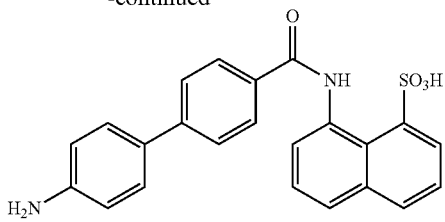

Hydrogenation was performed following a general procedure that is a modified version of the procedure from Kassack, M. U. et al. Eur. J. Med. Chem. 39:345-357 (2004). A mixture of 8-(4'-nitrobiphenyl-4-ylcarboxamido)naphthalene-1-sulfonic acid and 10% Pd on carbon in a solvent mixture of EtOH and DMF was hydrogenated ($H_2$ balloon) at 80° C. for 3.5 h. The reaction mixture was filtered via a short pad of Celite, concentrated in vacuo, and recrystallized from MeOH to afford the triethylamine salt of 8-(4'-aminobiphenyl-4-ylcarboxamido)naphthalene-1-sulfonic acid as a white solid (86%). HRMS (ESI) [M+H]$^+$ calcd. for $C_{23}H_{19}N_2O_4S^+$, 419.1060; found, 419.1058.

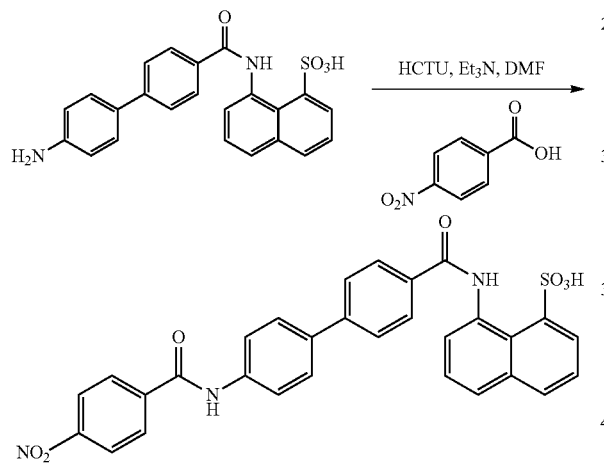

The general procedure for coupling described above was performed with 4-nitrobenzoic acid and 8-(4'-aminobiphenyl-4-ylcarboxamido)naphthalene-1-sulfonic acid to give the triethylamine salt of 8-(4'-(4-nitrobenzamido)biphenyl-4-ylcarboxamido)naphthalene-1-sulfonic acid (21041) as a yellow solid (87%) (99% pure by HPLC analysis (UV spectra at 254 nm)). HRMS [M−H]$^−$ calcd. for $C_{30}H_{21}N_3O_7S^−$, 566.1027; found, 566.1054. $^1$H NMR (500 MHz, DMSO-d$_6$): δ 12.64 (s, 1H), 10.75 (s, 1H), 8.85 (br, 1H), 8.39 (d, J=8.1 Hz, 2H), 8.36-8.16 (m, 6H), 8.02 (d, J=8.2 Hz, 1H), 7.95 (d, J=8.2 Hz, 2H), 7.91-7.81 (m, 5H), 7.59 (t, J=7.7 Hz, 1H), 7.49 (t, J=7.5 Hz, 1H), 3.07 (q, J=7.2 Hz, 6H), 1.15 (t, J=7.1 Hz, 9H); $^{13}$C NMR (125 MHz, DMSO-d$_6$): δ 165.1, 164.1, 149.2, 142.0, 141.8, 140.6, 138.8, 135.8, 134.9, 134.2, 133.3, 132.0, 129.4, 128.8, 127.5, 127.3, 126.0, 125.9, 125.4, 124.4, 124.1, 123.7, 123.0, 120.8, 45.7, 8.7; FTIR (neat) $v_{max}$ 3360, 3017, 2714, 1679, 1666, 1592, 1521, 1489, 1432, 1416, 1398, 1340, 1321, 1279, 1235, 1194, 1152, 1131, 1102, 1038, 1009, 929, 895, 864, 852, 824, 761, 708, 675, 661 cm$^{-1}$ Examples 2-9: Preparation of Additional Inhibitors The compounds of Examples 2-9 were formed using the general procedures for coupling described in Example 1. The syntheses were achieved via the same three steps using the biphenyl as an aromatic linker in the first step and different acids as coupling partners in the third step. Example 7 (21042) was simply synthesized in one step by hydrogenation of 21041. Example 2 (25041) and 3 (25441) were assembled using the corresponding differently substituted naphthyl rings. Table 1 lists the compounds according to Examples 1-9.

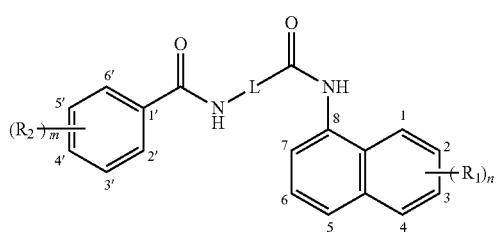

TABLE 1

| Example | S# | L | $R_1$ | $R_2$ |
|---|---|---|---|---|
| 1 | 21041 | biphenyl | 1-SO$_3$H | 4'-NO$_2$ |
| 2 | 25041 | biphenyl | 5-SO$_3$H | 4'-NO$_2$ |
| 3 | 25441 | biphenyl | 5-CO$_2$H | 4'-NO$_2$ |
| 4 | 24541 | biphenyl | 4-CO$_2$Me | 4'-NO$_2$ |
| 5 | 21045 | biphenyl | 1-SO$_3$H | 4'-CO$_2$Me |
| 6 | 21080 | biphenyl | 1-SO$_3$H | 3',4'-(N=N—NH)— |
| 7 | 21042 | biphenyl | 1-SO$_3$H | 4'-NH$_2$ |
| 8 | 11041 | benzene | 1-SO$_3$H | 4'-NO$_2$ |
| 9 | 51041 | 9H-fluorene | 1-SO$_3$H | 4'-NO$_2$ |

Example 10: Cell-Free Binding Assays

Compounds according to the disclosure were assessed for their ability to inhibit the binding of tagged ligands to plate-bound receptors using ELISA-type 96-well plate-based cell-free assays as described in the literature (see Margolles-Clark et al, J Mol Med 87:1133-1143 (2009); Margolles-Clark et al., Chem Biol Drug Des 76:305-313 (2010); Song et al., Br J Pharmacol 171:4955-4969 (2014); and Ganesan et al., Biochem Pharmacol 81:810-818 (2011)).

Recombinant receptors (hCD40:Fc, TNF-R1:Fc) and tagged ligands (hCD154, MegaCD40L, and TNF-α), were obtained from Enzo Life Sciences (San Diego, Calif.). Microtiter plates (Nunc F Maxisorp; 96-well) were coated overnight at 4° C. with 100 μL/well of Fc chimeric receptors diluted in PBS 7.2. This was followed by blocking with 200 μL/well of blocking solution (PBS 7.2, 0.05% Tween-20, 1% BSA) for 1 hour at room temperature. The plates were then washed twice using the washing solution (PBS 7.4, 0.05% Tween-20) and dried before the addition of the appropriate FLAG tagged/biotinylated ligands along with different concentrations of test compounds diluted in binding buffer (100 mM HEPES, 0.005% BSA pH 7.2) or protein-containing media (IMDM medium supplemented with 5% FBS) to give a total volume of 100 μL/well. Either anti-FLAG-HRP or streptavidin-HRP conjugate was used to detect the bound FLAG-tagged or biotinylated ligand, respectively. Plates were washed three times before the addition of 120 μL/well of HRP substrate TMB (3, 3', 5, 5'-tetramethylbenzidine) and kept in the dark for 15-30 min. The reaction was stopped using 30 μL 1M $H_2SO_4$, and the absorbance was read at 450 nm. Stock solutions of compounds at 10 mM in DMSO were used.

Typical concentrations used were as follows—receptors: 0.3 μg/mL for CD40, TNF-R1, and RANK; 0.6 μg/mL for BAFF-R, OX40, and 4-1BB; and 2 μg/mL for EGF-R ligands: 0.02 μg/mL for CD40L, TNFα, and RANKL; 0.2 μg/ml for BAFF, OX40L, 4-1BBL; and 0.3 μg/mL for EGF. Assays were done in duplicate or triplicate per plate and repeated at least three times; the averaged data were normalized and used for data fitting and analysis. Binding data were fitted using the standard log inhibitor versus response model in GraphPad Prism to determine the corresponding $IC_{50}$ values.

Figure 1B:
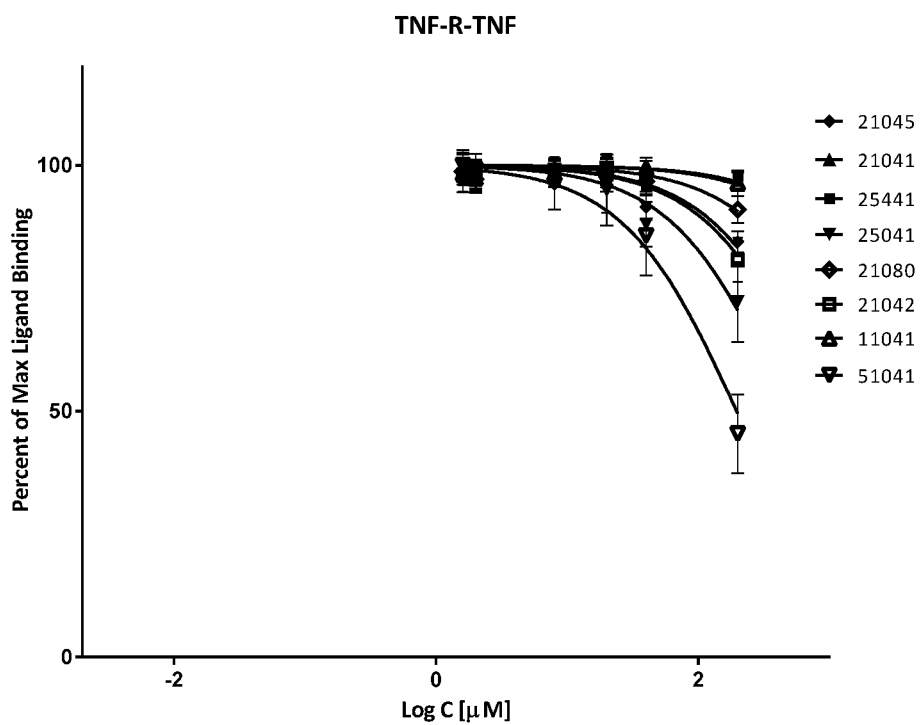
FIG. 1B shows lack of corresponding inhibition for human TNF-R-TNF α binding by the same compounds.

FIG. 1A shows the results obtained for several compounds of the disclosure, 11041, 21041, 21042, 21045, 21080, 25041, 25441, and 51041, for the CD40-CD40L assay. Direct red 80 (DR80, a compound previously shown to be active in this assay (see Margolles-Clark et al, J Mol Med 87:1133-1143 (2009)) was included as positive control. FIG. 1B shows corresponding results obtained for the TNF-R-TNFα assay. Data are average±SD (normalized to percent binding) for n=3 independent experiments with triplicates for each condition and were fitted with standard binding curves using GraphPad Prism software. Example 10 shows that several of the present compounds are about an order of magnitude more active then DR80 in inhibiting the CD40-CD40L interaction; e.g., half-maximal inhibitory concentrations ($IC_{50}$s) of 0.14, 0.31, and 0.36 μM for 21045, 21041, and 25441 respectively vs. 2.26 μM for DR80. Example 10 also shows that all of the present compounds are inactive in inhibiting the TNF-R-TNFα interaction, demonstrating specificity of the compounds for inhibiting the CD40-CD40L interaction.

Example 11: Inhibition of CD40L-Induced NF-κB Activation

Activities of the compounds of the disclosure were confirmed in cell-based assays. As a first example, TNF-R1 and CD40 expressing sensor cells (HEK-Blue; InvivoGen, San Diego, Calif.) were used as described in the literature (see Song et al., Br J Pharmacol 171:4955-4969 (2014) and Cechin et al., Steroids 85:36-43 (2014)).

Figure 2:
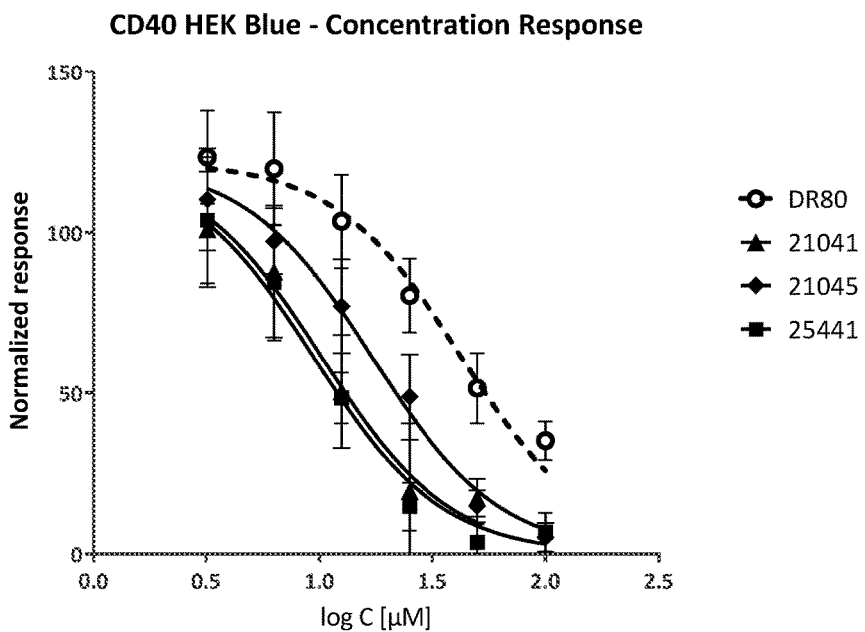
FIG. 2 shows concentration-dependent inhibition of CD40L-induced NF-κB activation in CD40 sensor cells (HEK Blue, InvivoGen) by 21041, 21045, and 25441 with DR80 as positive control.

Cells were maintained in DMEM at 80% confluence for each experiment. Cells were trypsinized and re-suspended in the same medium with 1% FBS and seeded on 96-well microtiter plates at a density of $1 \times 10^5$ cells/well in the absence and presence of various concentrations of compounds diluted in the same media. For ligand mediated stimulation, final concentrations of recombinant human TNFα (2 ng/mL) and CD40L (20 ng/mL) were maintained in the wells for this purpose. After 18-hour incubation at 37° C., 20 μL supernatant of each well were taken and added to another 96-well microtiter plate containing 180 μL/well of QUANTI-Blue (InvivoGen, CA). The level of SEAP was determined after 30-minute incubation at 37° C. by reading at 625 nm using a spectrophotometer. FIG. 2 shows representative results for compounds of the present invention. Data are average±SD (normalized to CD40L-activated cells alone) for n=4 independent experiments with duplicates for each condition. Example 11 shows that while the compounds are less active in this cell-based assay then in the cell-free binding inhibition assay, the compounds of the disclosure show promising activity in concentration-dependently inhibiting the CD40L-induced activation of NF-κB in these cells (i.e., $IC_{50}$s of 17, 10, and 9 μM here for 21045, 21041, and 25441, respectively), and are more active than DR80 ($IC_{50}$ of 42.7 μM). Furthermore, inhibition is specific for CD40L-stimulation; the same compounds did not inhibit TNFα-induced stimulation of the same cells.

Example 12: Inhibition of the CD40L-Induced THP-1 Cell Activation

As a further assessment, the ability of the compounds of the disclosure to inhibit the CD40L-induced activation of THP-1 cells, which can serve as surrogate dendritic cells, was evaluated using an assay as described previously (see Margolles-Clark et al, J Mol Med 87:1133-1143 (2009)).

THP-1 human myeloid cells obtained from American Type Culture Collection (ATCC; Manasses, Va.) were cultivated in RPMI media 1640 supplemented with 10% FBS, 100 U/mL penicillin, and streptomycin 100 μg/mL to a density of $1 \times 10^6$ cells/mL. Cells were centrifuged and cultured in the same medium without FBS for a period of 24 hours. Starved cells were placed in fresh medium without FBS and stimulated with 0.5 μg/mL of rhCD154 (MegaCD40L; Enzo Life Sciences), in the presence of various concentrations of test compounds. After 48 h, cells were labeled with biotin conjugated monoclonal anti-human CD40 antibody (clone LOB7/6) (LifeSpan BioSciences, Seattle, Wash.), detected with allophycocyanin-eFluor™ 780 streptavidin (eBioscience, San Diego, Calif.), and labeled with monoclonal anti-human HLA-DR antibody APC-Alexa Fluor® 750 (clone LN3) (eBioscience, San Diego, Calif.). All cultivations were carried out for 48 h at 37° C., 90% humidity, and 5% $CO_2$. Stained THP-1 cells were analyzed using a BD LSR II Flow Cytometer (BD Biosciences, San Jose, Calif.). Cell surface markers were quantified in live cells only after gating out 4',6-diamidino-2-phenylindole (DAPI) labeled cells. All experiments were repeated at least three times.

Figure 3:
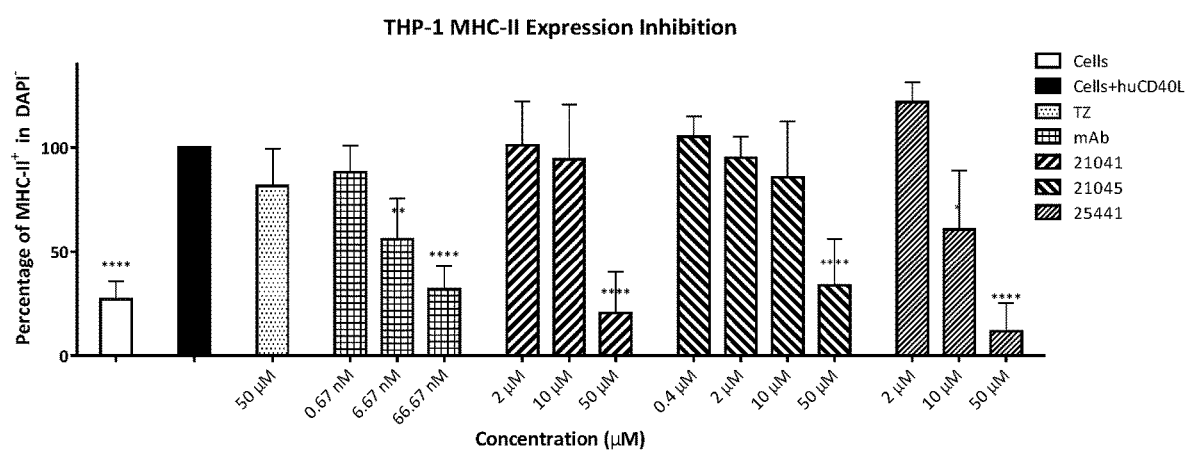
FIG. 3 shows concentration-dependent inhibition of CD40L-induced MHC-II expression in human THP-1 cells by 21041, 21045, and 25441 with tartrazine (TZ) and an anti-CD40L antibody (mAb) included as negative and positive controls, respectively.

FIG. 3 shows representative results of compounds of the disclosure. Data are average±SD in live (DAPI⁻) cells from five independent experiments and were analyzed by ****p one-way ANOVA followed by Dunnett's multiple comparison test, *$p<0.05$, $p<0.01$, **$p<0.0001$ vs. cells+ huCD40L. FIG. 3 illustrates that several compounds of the present disclosure (i.e., 21041 and 25441) concentration-dependently inhibit this CD40L-induced activation with $IC_{50}$s in the 10 μM range. Thus, Example 12 shows inhibition of the CD40L-induced THP-1 cell activation by compounds of the disclosure.

Example 13: Inhibition of the CD40L-Induced Human B-Cell Proliferation Assay Because CD40 stimulation is an important signal for B cell proliferation, soluble CD40L can concentration-dependently induce the proliferation of human B cells. The CD40L-induced proliferation of human CD19⁺ B cells was used here to assess the inhibitory effect of selected compounds using the method as described before (see Margolles-Clark et al, J Mol Med 87:1133-1143 (2009) and Margolles-Clark et al., Biochem Pharmacol 77:1236-1245 (2009)).

Inhibition of cell proliferation was determined in freshly isolated human CD19⁺ B cells using the colorimetric cell proliferation ELISA BrdU kit from Roche Applied Science (Indianapolis, Ind.). B cells were isolated from the PBMC as follows. Briefly, cells were washed three times with medium (RPMI 1640) and incubated for 20 min at 4° C. with 20 μL/$10^7$ cells of anti-CD19 Microbeads (Miltenyi Biotech, Bergisch Gladbach, Germany), according to the MiniMacs protocol (Miltenyi Biotech). Cells were then purified using magnetic columns. At the end of the purification procedure, cells were found to be almost exclusively (>90%) CD19+ by cytofluorimetric analysis. Cells were cultured in 96 wells plates (100 μL/well) at a cell density of $2\times10^5$ cells/mL in IMDM medium supplemented with 5% FBS, 100 U/mL penicillin, streptomycin 100 μg/mL, insulin-transferrin-selenium-G (all materials from Invitrogen, San Diego, Calif.) and 10 μg/mL of rhIL-4 (R&D Systems). Cells were activated with 0.1 μg/mL of rhCD154 (MegaCD40L, Enzo Life Sciences) in the presence of various concentrations of test compounds. After 48 h, BrdU labeling solution was added as recommended, and cells were cultivated for another 48 h. Detection of incorporated BrdU was carried out following the instructions of the ELISA BrdU kit.

Figure 4:
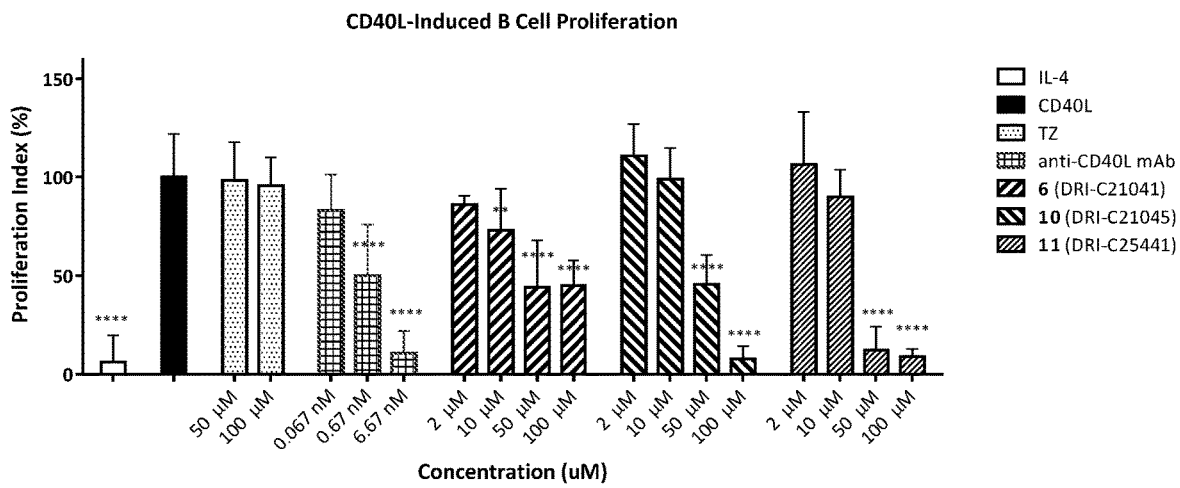
FIG. 4 shows concentration-dependent inhibition of the CD40L-induced human CD19+ B-cell proliferation by 21041, 21045, and 25441 with tartrazine (TZ) and an anti-CD40L antibody (mAb) included as negative and positive controls, respectively.

As shown in FIG. 4, this assay confirmed that this effect is concentration-dependently inhibited by the corresponding mAb in the nM range, and also by some of the present compounds (e.g., 21045 and 25441) with $IC_{50}$s approximately in the ~20 μM range. Data are average±SD for n=3 independent experiments with triplicates for each condition using a standard BrdU assay (Roche). Data were analyzed by one-way ANOVA followed by Dunnett's multiple comparison test, $p<0.01$, $p<0.0001$ vs. CD40L. This result is similar to what was observed in the other cell-based assays. The inhibitory effect at these concentrations is not toxicity related, as the viability of cells was not significantly affected at these concentrations of the test compounds (see FIG. 6). Tartrazine, a structurally related compound that was inactive in the binding assay, was used as a negative control, and it indeed had no proliferation inhibiting activity. Data are average±SD of three experiments in duplicate and were analyzed by one-way ANOVA followed by Dunnett's multiple comparison test, **$p<0.0001$ vs. cells only.

Thus, Example 12 shows inhibition of the CD40L-induced human B-cell proliferation by compounds of the disclosure.

Example 14: Inhibition of the CD40L-Induced Human B-Cell Functionality

Activities in blocking CD40L-induced effects were assessed in a human B cell functional assay that quantitates B-cell function by measuring AID activation via a downstream fluorescent marker using flow cytometry. Activation-induced cytidine deaminase (AID) is necessary for both class switch recombination (CSR) and somatic hypermutation (SHM) of Ig genes, which are important for the generation of high-affinity antibodies and robust humoral immune response (see Frasca et al., Methods Mol Biol 1343:107-114 (2015)). AID is encoded by the aicda gene that is exclusively expressed in B cells and is necessary for opening the DNA molecule in the switch (S) regions in order to allow CSR. Engagement of CD40, which is constitutively expressed on the surface of B cells, with CD40L on T cells has been shown to positively regulate the expression of AID in B cells through activation of NF-κB signaling pathway. To further validate the activity of the present compounds, an aicda-lentiviral construct containing the promoter and enhancer region of aicda fused to the reporter Ds-Red was generated and used to transfect human B cells isolated from healthy donors. In these cells, regulation of AID expression through CD40-CD40L signaling following incubation at different conditions were evaluated by Ds-Red level assessed via flow cytometry.

B cells were isolated using anti-CD19 Microbeads (Miltenyi Biotech) from PBMC collected from healthy donors, and they were purified using magnetic columns. These B cells were than transfected with an aicda-DsRed vector using a lentiviral protocol, $1.25\times10^5$ cells/mL of transfected B cells were stimulated with IL-4 at 0.2 μg/mL and CD40 ligand at 0.2 μg/mL in IMDM media with 10% FBS. In addition, various concentrations of candidate compounds diluted in the same media were added along with the described condition above. Also, 1 μg/ml of CpG was used as positive control for activation. After culture for 2 days at 37° C. and 5% $CO_2$, B cells were collected, and AID activation level as represented by the level of Ds-Red expression was assessed by flow cytometry using BD LSRFortessa cell analyzer.

Figure 5:
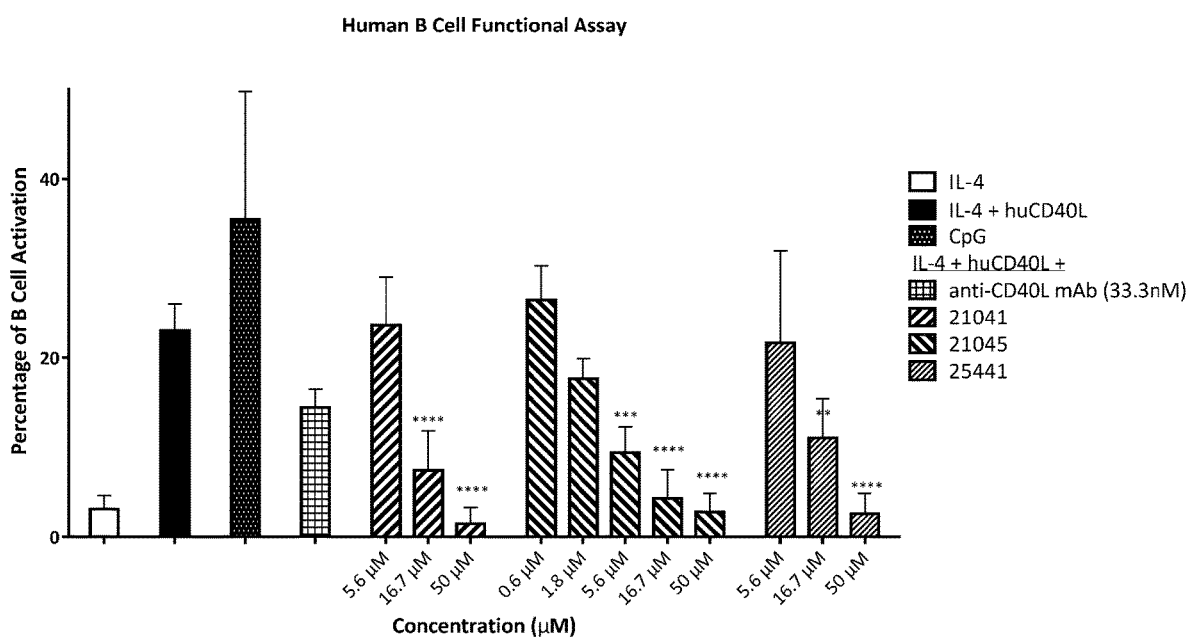
FIG. 5 shows concentration-dependent inhibition of the CD40L-induced human B-cell function (activation-induced cytidine deaminase, AID, activation quantified via a fluorescent marker detected by flow cytometry) by 21041, 21045, and 25441 assessed in a flow cytometry experiment with an anti-CD40L antibody (mAb; 33.3 nM) included as positive control.

FIG. 5 shows the results obtained here, which also include an anti-CD40L antibody (mAb) as positive control. The assay clearly confirms concentration-dependent inhibition of CD40L-induced activation with $IC_{50}$s 4.5, 13.2, and 15.9 μM for representative compounds of the disclosure, 21045, 21041, and 25441, respectively. These are important results as they were obtained in freshly isolated human B cells, a model particularly relevant for autoimmune diseases, and they assess effects on function not just proliferation or viability. Data are average±SD for three independent experiments and were analyzed by one-way ANOVA followed by Dunnett's multiple comparison test, *$p<0.05$, $p<0.01$, **$p<0.0001$.

Thus, Example 14 shows inhibition of the CD40L-induced human B-cell functionality by compounds of the disclosure.

Example 15: Assessment of Cytotoxicity

Figure 6:
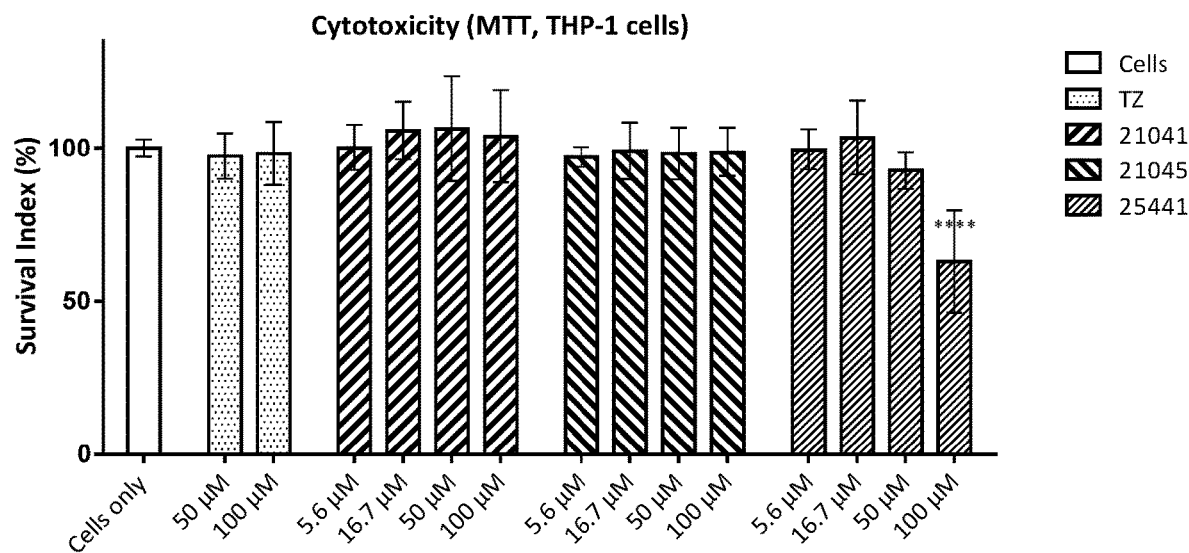
FIG. 6 shows a toxicity assessment of 21041, 21045, and 25441 using a standard MTT cytotoxicity assay in THP-1 cells.

To ensure that compounds are suitable to be developed as possible therapeutics it is important that they have an adequate therapeutic index, i.e., sufficient separation between their effective and toxic doses. Therefore, cytotoxicities were also evaluated to eliminate those compounds that are likely to be unacceptably toxic. As a first evaluation, cytotoxicities were assessed using a standard in vitro toxicology assay kit (MTS). For the MTS assay, THP-1 human myeloid cells obtained from American Type Culture Collection (ATCC; Manasses, Va.) were cultured in RPMI-1640 medium (Invitrogen, CA) with 10% FBS (v/v; Invitrogen) and 1% penicillin-streptomycin (v/v; Invitrogen). Cells were centrifuged and re-suspended in the same medium without FBS for a 24 h starvation. Then cells were added to a 96-well microtiter plate at a density of 50,000 cells/well in the absence or presence of various concentrations of compounds diluted in the same media. The plate was incubated at 37° C. for 48 hours. 20 μL per well of MTS tetrazolium (Promega, Madison, Wis.) was added to the culture after treatments, and cells were incubated at 37° C. for another 0.5 h. Formazan levels were measured using a plate reader at 490 nm. FIG. 6 shows the toxicity assessment of selected compounds of the disclosure, 21041, 21045, and 25441. Thus, Example 15 shows compounds of the disclosure are suitable for therapeutic use in the concentration range tested here.

Example 16: Activity in a Skin Transplant Model

Figure 7:
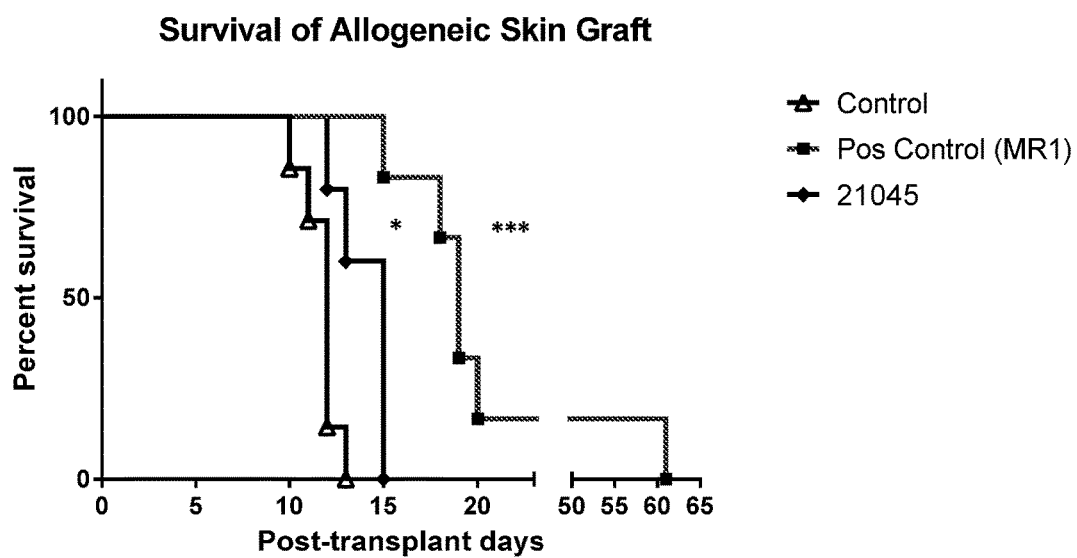
FIG. 7 shows prolongation of skin allograft by compound 21045 in C57BL6 mice transplanted with Balb/c skin grafts and treated with 250 µg of CTLA4-Ig (days 0, 2, 4, and 6) plus CD40L antibody (MR-1; 250 µg; days 0, 2, 4, and 6) or 21045 (30 mg/kg; daily, s.c. in 20% HPβCD).

As a first in vivo test of the immunomodulating ability of the present compounds, the ability of compound 21045 to cause prolongation of skin allograft survival was examined. Full-thickness ear skins from donor mice (Balb/c, Jackson Laboratory; Bar Harbor, Me.) were transplanted onto the dorsal thorax of recipient mice (C57BL/6, Jackson Laboratory) by placing them on ~1 cm diameter graft beds and securing with bandages. Following a protocol from Pinelli, D. F. et al. Am. J. Transplant. 13:3021-3030 (2013), mice were treated with CTLA4-Ig (Orencia; Bristol-Myers Squibb, New York City, N.Y.; 250 µg, days 0, 2, 4, and 6 plus either CD40L antibody (MR-1; Bio X Cell; West Lebanon, N.H.; 250 µg, days 0, 2, 4, and 6) or 21045 (30 mg/kg) (daily, s.c.). Because of solubility limitations, 21045 was administered in 20% w/v hydroxypropyl-β-cyclodextrin (HPβCD) solution. Bandages were removed on day 7 post-transplant and grafts were monitored and scored daily. Skin grafts were rated visually (0: perfect skin, 1:10%-50% necrotic, 2:75% necrotic, 3:100% necrotic), and the first score of 3 was considered as the day of rejection. Mice treated with CTLA4-Ig alone rejected skin grafts with a mean survival time (MST) of 12.0 days. Addition of 21045 prolonged survival in a statistically significant manner (MST of 15 days), but less than the positive control MR-1 (MST of 19 days) (FIG. 7). Data are with a total of 5-8 mice per group. *p<0.05, ***p<0.001 compared to CTLA4-Ig alone. Skin transplants are among the most stringent transplants as they are known to generate higher immune response than, liver, heart, or kidney transplants; therefore, even small prolongations are indicative of immunomodulatory potential. Thus, Example 16 shows that 21045, a representative compounds of the disclosure, has immunomodulatory activity in an in vivo rodent model.

Inhibitory data ($IC_{50}$, µM) for various compounds is presented in Table 2.

or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

TABLE 2

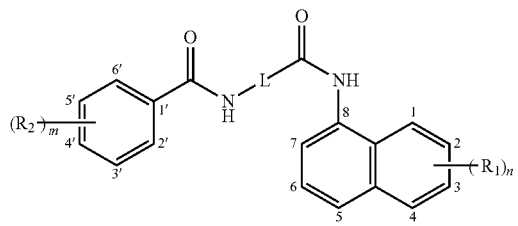

(I)

| Table 2 Example | S# | L | $R_1$ | $R_2$ | $IC_{50}$ CD40 | $IC_{50}$ OX40 | $IC_{50}$ B Cell |
|---|---|---|---|---|---|---|---|
| 1 | 21041 | biphenyl | 1-$SO_3H$ | 4'-$NO_2$ | 0.3 | 605.5 | 13.2 |
| 2 | 25041 | biphenyl | 5-$SO_3H$ | 4'-$NO_2$ | 2.3 | 7.0 | |
| 3 | 25441 | biphenyl | 5-$CO_2H$ | 4'-$NO_2$ | 0.4 | 2.7 | 15.9 |
| 4 | 24541 | biphenyl | 4-$CO_2Me$ | 4'-$NO_2$ | 916 | 6564 | |
| 5 | 21045 | biphenyl | 1-$SO_3H$ | 4'-$CO_2Me$ | 0.1 | 135.1 | 4.5 |
| 6 | 21080 | biphenyl | 1-$SO_3H$ | 3',4'-(N=N—NH)— | 1.0 | 26.3 | |
| 7 | 21042 | biphenyl | 1-$SO_3H$ | 4'-$NH_2$ | 301.0 | 12.8 | |
| 8 | 11041 | benzene | 1-$SO_3H$ | 4'-$NO_2$ | 341.6 | >5000 | |
| 9 | 51041 | 9H-fluorene | 1-$SO_3H$ | 4'-$NO_2$ | 11.2 | 2 | |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components

What is claimed:

1. A compound of formula (I):

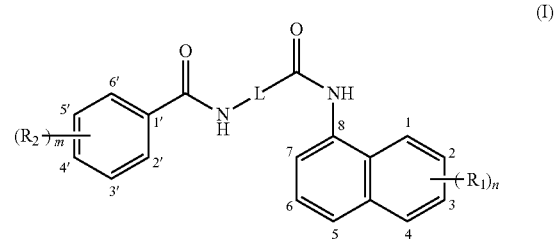

(I)

wherein
L has a structure:

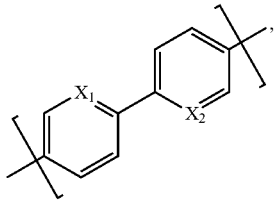

and $X_1$ and $X_2$ are each independently CR or N;
each $R_1$ independently is $SO_3H$, —$CO_2R$, or $NO_2$;
each $R_2$ independently is —$NO_2$, —$CO_2R$, —$NH_2$, —Cl, —F, —$CF_3$, phenyl, or phenyl substituted with one or more of —$NO_2$, —$CO_2R$, —$NH_2$, —Cl, —F, or —$CF_3$, and/or two adjacent $R_2$ together form —(N=N—NH)—;
each R independently is H, $C_{1-5}$ alkyl, or —O—$C_{1-5}$ alkyl;
n is 1, 2, 3, or 4; and
m is 1, 2, 3, or 4;
or a pharmaceutically acceptable salt thereof.

2. The compound of claim 1, wherein at least one of $X_1$ and $X_2$ is CR.

3. The compound of claim 2, wherein R is H.

4. The compound of claim 1 wherein at least one of $X_1$ and $X_2$ is N.

5. The compound of claim 1, wherein at least one $R_1$ is $SO_3H$ or $CO_2R$.

6. The compound of claim 5, wherein R is selected from $C_{1-5}$ alkyl and H.

7. The compound of claim 1, wherein the compound-is substituted with $R_1$ at position 1, 4, 5, or a combination thereof.

8. The compound of claim 1, wherein $R_1$ is 1-$SO_3H$, 5-$SO_3H$, 4-$CO_2Me$, 5-$CO_2H$, or a combination thereof.

9. The compound of claim 1, wherein at least one $R_2$ is —$NO_2$, $NH_2$, or —$CO_2R$.

10. The compound of claim 9, wherein R is selected from $C_{1-5}$ alkyl and H.

11. The compound of claim 1, wherein two adjacent $R_2$ together form —(N=N—NH)—.

12. The compound of claim 1, wherein the compound is substituted with $R_2$ at the 4' position or the 3' position.

13. The compound of claim 1, wherein $R_2$ is 4'-$NO_2$, 4'-$CO_2Me$, 4'-$NH_2$, 3',4'-(N=N—NH)—, 4'-$C_6H_4$-(4"-$NO_2$), or 4'-$C_6H_4$-(4"-$CO_2R$).

14. The compound of claim 1 selected from the group consisting of:

21041

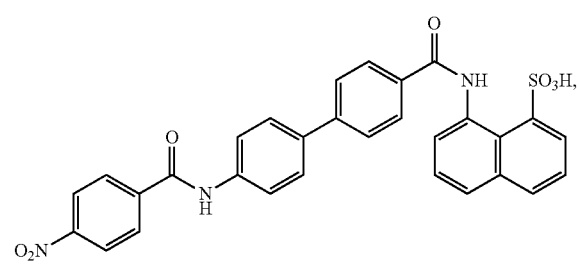

-continued

51041

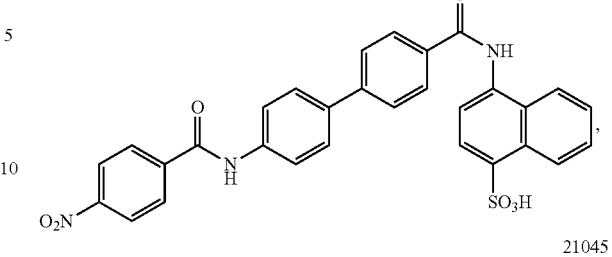

21045

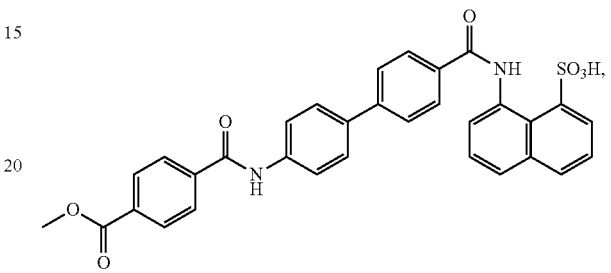

21042

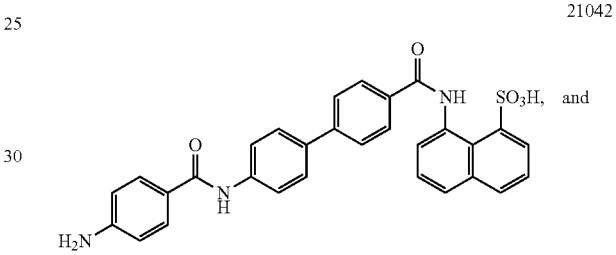

25441

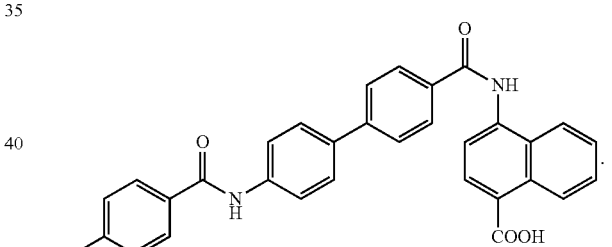

15. A pharmaceutical composition comprising the compound of claim 1 and a pharmaceutically acceptable carrier.

16. A method of modulating TNF superfamily costimulatory interactions in a subject, comprising administering to the subject a compound according to claim 1.

17. The method of claim 16, wherein the compound or composition modulates one or more interactions selected from the group consisting of CD40-CD40L, TNF-$R_1$-TNF-α, CD80(137)-CD28, CD80(137)-CD152(CTLA4), CD86 (67-2)-CD28, CD86-CD152, CD27-CD70, CD137(4-1BB)-4-1BBL, HVEM-LIGHT(CD258), CD30-CD30L, GITR-GITRL, BAFF-R(CD268)-BAFF(CD257), RANK (CD265)-RANKL(CD254), OX40(CD134)-OX40L (CD252), and combinations thereof.

18. A method of treating an inflammatory or immune system disorder in a subject in need thereof, comprising administering to the subject a therapeutically effective amount of the compound of claim 1.

19. The method of claim 18, wherein the subject is a nonautologous organ or cell transplant recipient and suffers from rejection of the nonautologous organ or cell transplant.

20. The method of claim 18, wherein the inflammatory or immune system disorder comprises rheumatoid arthritis, systemic lupus erythematosus (SLE), multiple sclerosis (MS), type I (juvenile) diabetes, mixed connective tissue disease MCTD, Celiac disease, Crohn's disease, ulcerative colitis, Grave's disease, Sjögren's syndrome, dermatomyositis, psoriasis, scleroderma, polymyositis, vasculitis, Wegener's granulomatosis, alopecia areata, chronic inflammatory disease, autoimmune disease, neurodegenerative disorder, graft-versus-host disease, cancer, atherosclerosis, a rejection of a nonautologous organ transplant, or a rejection of nonautologous cell transplant.

* * * * *